US009226821B2

United States Patent
Matheny

(10) Patent No.: US 9,226,821 B2
(45) Date of Patent: *Jan. 5, 2016

(54) EXTRACELLULAR MATRIX MATERIAL CONDUITS AND METHODS OF MAKING AND USING SAME

(71) Applicant: CorMatrix Cardiovascular, Inc., Roswell, GA (US)

(72) Inventor: Robert G. Matheny, Norcross, GA (US)

(73) Assignee: CorMatrix Cardiovascular, Inc., Roswell, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/200,396

(22) Filed: Mar. 7, 2014

(65) Prior Publication Data
US 2014/0188218 A1    Jul. 3, 2014

Related U.S. Application Data

(63) Continuation of application No. 13/480,347, filed on May 24, 2012, now Pat. No. 8,845,719.

(51) Int. Cl.
*A61F 2/24* (2006.01)
*A61L 27/36* (2006.01)
*A61L 2/00* (2006.01)
*A61L 27/38* (2006.01)
*A61L 27/54* (2006.01)

(52) U.S. Cl.
CPC ............ *A61F 2/2412* (2013.01); *A61L 2/0094* (2013.01); *A61L 27/3633* (2013.01); *A61L 27/3687* (2013.01); *A61L 27/3691* (2013.01); *A61L 27/3873* (2013.01); *A61L 27/3882* (2013.01); *A61L 27/54* (2013.01); *A61F 2/24* (2013.01); *A61L 2430/20* (2013.01); *A61L 2430/40* (2013.01)

(58) Field of Classification Search
CPC ..... A61F 2/24; A61F 2/2412; A61L 2430/20; A61L 2430/40; A61L 27/3629; A61L 27/3633
See application file for complete search history.

(56) References Cited

U.S. PATENT DOCUMENTS

2010/0233235 A1* 9/2010 Matheny et al. ............. 424/423

* cited by examiner

*Primary Examiner* — Brian Dukert
(74) *Attorney, Agent, or Firm* — Francis Law Group

(57) ABSTRACT

Extracellular matrix (ECM) valve conduits are disclosed. Methods for regenerating atrioventricular valves to replace defective atrioventricular valves within a heart of a subject using the ECM valve conduits are also disclosed. Methods of sterilizing and decellularizing an ECM material are also disclosed.

2 Claims, 19 Drawing Sheets

EXTRACELLULAR MATRIX MATERIAL CONDUITS AND METHODS OF MAKING AND USING SAME

CROSS-REFERENCE TO RELATED APPLICATIONS

This application is a continuation of U.S. application Ser. No. 13/480,347, filed on May 24, 2012, which claims the benefit of the filing dates of U.S. Provisional Patent Application No. 61/490,693, filed on May 27, 2011, U.S. Provisional Patent Application No. 61/490,873, filed on May 27, 2011, U.S. Provisional Patent Application No. 61/491,723, filed on May 31, 2011, and U.S. Provisional Patent Application No. 61/650,911, filed on May 23, 2012, each of which is hereby incorporated by reference herein in its entirety.

FIELD OF THE INVENTION

The invention relates to extracellular matrix (ECM) material conduits and methods of using such ECM material conduits to regenerate atrioventricular (AV) valves within a heart of a subject.

BACKGROUND OF THE INVENTION

There are many known types of replacement heart valves. The selection of a particular type of replacement heart valve depends on factors such as the location of the valve, the age and other specifics of the patient, and the surgeon's experiences and preferences. Commonly used replacement heart valves can be classified in the following three groups: mechanical valves; allograft tissue valves; and xenograft tissue valves.

Mechanical heart valves, including, for example and without limitation, caged-ball valves, bi-leaflet valves, and tilting disk valves are typically attached to a sewing ring so that the valve prosthesis can be sutured to the patient's native tissue to hold the mechanical valve in place postoperatively. Although mechanical heart valves have advantageous long-term durability, these mechanical valves also have a propensity to cause the formation of blood clots in a patient. If such blood clots form on the mechanical valve, they may preclude the valve from opening or closing correctly or, more importantly, may disengage from the valve and embolize to the brain, causing an embolic stroke. Thus, the patients who receive such mechanical valves are typically required to take systemic anticoagulant drugs for the rest of their lives. In addition to being expensive, these anticoagulant drugs can themselves be dangerous in that they can cause abnormal bleeding in the patient that can lead to a hemorrhagic stroke.

Allograft tissue valves are harvested from human sources, such as human cadavers. Unlike mechanical heart valves, allograft tissue valves typically do not promote blood clot formation and, therefore, avoid the need for prescribing an anticoagulant medication for the patient. However, allograft tissue valves are not available in sufficient numbers to satisfy the needs of all patients who need new heart valves. Furthermore, there have been significant complications when allograft tissue valves have been used to replace atrioventricular (AV) valves within a subject. Moreover, allograft tissue valves can be more difficult to implant than mechanical valves or xenograft valves. Because of these difficulties in implantation, the operative risk associated with allograft tissue valves is often greater than the operative risks associated with mechanical valves and xenograft valves.

Xenograft tissue valves are formed from non-human tissue sources, such as cows or pigs. Most known xenograft tissue valves are constructed by sewing and/or constructing valve leaflets from a non-human tissue source and then securing the leaflets within a patient's heart using a stent and/or a sewing ring. These xenograft tissue valves are less likely to cause blood clot formation than comparable mechanical valves, and therefore, patients that receive xenograft tissue valves are not always required to take anticoagulant medications. However, xenograft tissue valves are prone to calcification and lack the long-term durability of mechanical valves and, consequently, require frequent replacement as compared to mechanical valves. One factor that may contribute to these failures is the chemical treatment that the xenograft tissue valves typically undergo to reduce antigenicity of the animal tissue. Without these chemical treatments, xenograft tissue valves can trigger an immune response in a patient, which can lead to rejection of the tissue valve by the patient. Another factor that may contribute to the lack of durability of the xenograft tissue valves is the presence of a stent and/or sewing ring, which can prevent the xenograft tissue valve from accurately approximating the anatomy of a normal heart valve.

Known tissue conduits, including those described in U.S. Pat. Nos. 5,480,424 and 5,713,950, both of which are expressly incorporated herein by reference in their entirety, suffer from various limitations, including many of the limitations of known xenograft tissue valves. For example, known tissue conduits suffer from antigenicity of the conduits, which is typically addressed using chemical treatments that lessen post-implantation durability of the conduit. Additionally, these known conduits are rapidly degraded within a patient's heart such that they can only serve as competent heart valve replacements for a matter of months.

Thus, what is needed in the art is a readily available, highly durable, and affordable tissue prosthesis that can be easily implanted to regenerate an anatomically accurate AV valve within the heart of a subject. There is a further need in the art for a sterile, acellular tissue prosthesis that can be implanted to regenerate an AV valve within the heart of a subject.

SUMMARY OF THE INVENTION

Extracellular matrix (ECM) material conduits are disclosed. In one aspect, a disclosed ECM material conduit defines a lumen and has an inlet portion and an outlet portion. The inlet portion of the ECM material conduit includes an inlet of the lumen. The outlet portion of the ECM material conduit includes an outlet of the lumen. The inlet portion and the outlet portion of the ECM material conduit can each have an outer circumference. The ECM material conduit is sterile and acellular. Methods of regenerating an atrioventricular (AV) valve to replace a defective AV valve within a heart of a subject are also disclosed. In one aspect, the methods include removing the defective AV valve from the heart of the subject. The methods also include implanting an ECM material conduit within the heart of the subject to regenerate a functional AV valve.

BRIEF DESCRIPTION OF THE FIGURES

These and other features of the preferred embodiments of the invention will become more apparent in the detailed description in which reference is made to the appended drawings wherein:

FIG. 4 includes markings corresponding to particular measurements that were performed on various native porcine and human tri-cuspid valves.

FIG. 5 displays the ECM material conduit in a closed position within an in vitro model of the right heart.

FIG. 6(a) depicts the ECM material conduit one month following the operation with the valve in a closed position. FIG. 6(b) depicts the ECM material conduit immediately post-operatively with the valve in an open position. FIG. 6(c) depicts the ECM material conduit immediately post-operatively with the valve in a closed position.

FIG. 7(a) shows regeneration at 3 months. FIG. 7(b) shows regeneration at 5 months. FIG. 7(c) shows regeneration at 8 months. FIG. 7(d) shows regeneration at 12 months.

FIG. 9 shows the DNA content of each SIS composition following sterilization.

FIG. 10 shows the percentage of DNA that was removed from each SIS composition following sterilization, as compared to raw, unprocessed SIS.

FIG. 11 shows the bFGF content of each SIS composition (normalized by dry weight of samples) following sterilization.

FIG. 12 shows the active TGF-β content of each SIS composition (normalized by dry weight of samples) following sterilization.

FIG. 13 shows the bFGF content for each SIS composition (normalized by dry weight of samples) following rapid depressurization.

FIG. 14 shows the tensile strength measured for each SIS composition following sterilization.

FIG. 15 shows the bFGF enzyme-linked immunosorbent assay (ELISA) results for each SIS composition (normalized by dry weight of samples) following sterilization and/or decellularization.

DETAILED DESCRIPTION OF THE INVENTION

Figure 1:
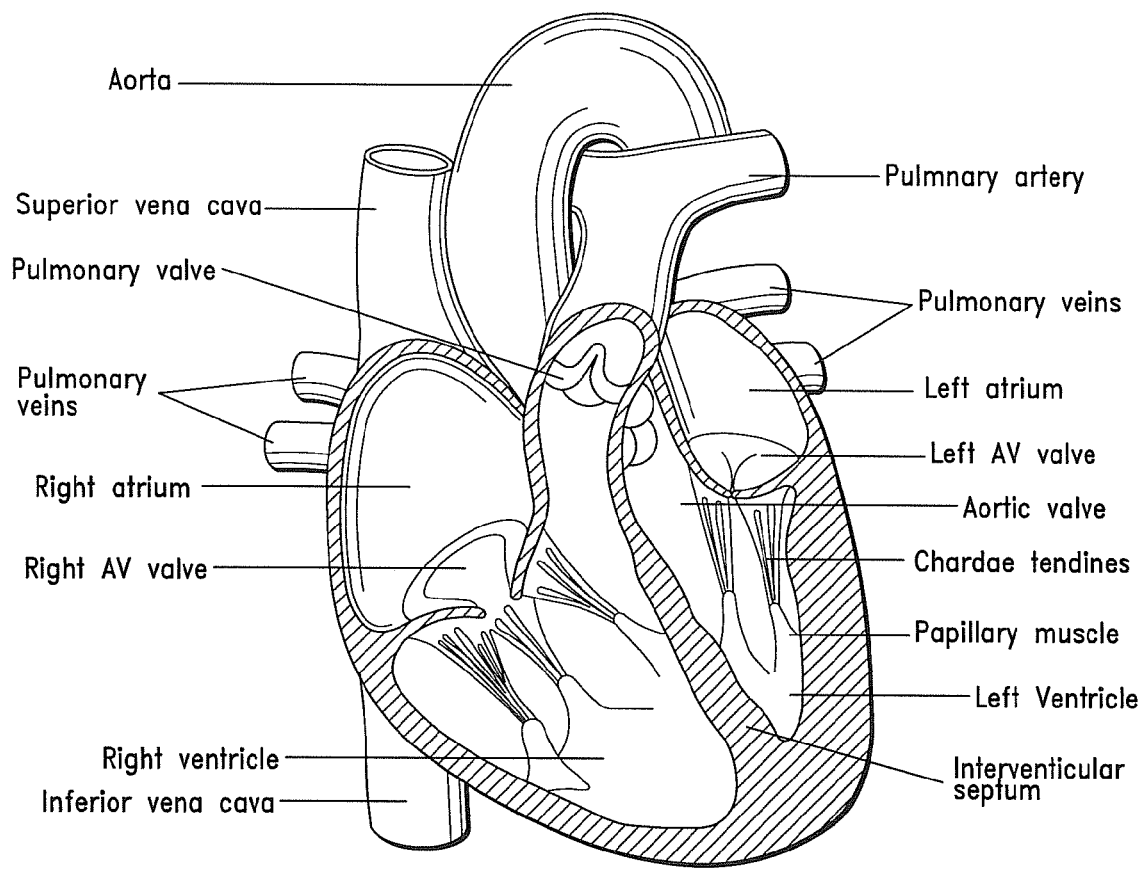
FIG. 1 is a cut-away view of a human heart.

The present invention may be understood more readily by reference to the following detailed description, examples, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to an "attachment point" can include two or more such attachment points unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" and "optionally" mean that the subsequently described event or circumstance may or may not occur, and that the description includes instances where said event or circumstance occurs and instances where it does not.

The word "or" as used herein means any one member of a particular list and also includes any combination of members of that list.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Without the use of such exclusive terminology, the term "comprising" in the claims shall allow for the inclusion of any additional element—irrespective of whether a given number of elements is enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject can be used interchangeably with the term "patient."

As used herein, the term "circumference" refers to the perimeter of, or the length measurement of the boundary defined by, a closed planar figure. Optionally, as used herein, a "circumference" can correspond to the perimeter of a closed planar circle. However, it is contemplated that a "circumference" can correspond to the perimeter of any closed planar figure, such as, for example and without limitation, an oval, square, rectangular, trapezoidal, or nonsymmetrical closed planar figure. For example, as used herein, an outer "circumference" of a conduit corresponds to the perimeter of the closed planar figure defined by an outer surface of the conduit at a particular location along the longitudinal axis of the conduit.

As used herein, the term "frusto-conical" refers to the shape of a conical frustum, which corresponds to the shape of a cone that has had its tip truncated by a plane parallel to its base. Thus, as used herein, a "frusto-conical" conduit has a substantially circular cross-section that varies in diameter along its longitudinal axis. The "frusto-conical" conduits disclosed herein have inlet portions and outlet portions that each have outer circumferences. Optionally, the outer circumference of the outlet portion of a disclosed "frusto-conical" conduit can be greater than the outer circumference of the inlet portion of the "frusto-conical" conduit. Alternatively, the outer circumference of the outlet portion of a disclosed "frusto-conical" conduit can be less than the outer circumference of the inlet portion of the "frusto-conical" conduit. In exemplary aspects, the outer circumference of the outlet portion of a disclosed "frusto-conical" conduit can be substantially equal to the outer circumference of the inlet portion of the "frusto-conical" conduit.

As used herein, the term "acellular" is meant to describe extracellular matrix compositions that are at least 80% decellularized such that the extracellular matrix composition is at least 80% without cells and/or cellular remnants. In some exemplary aspects described herein, the term "acellular" can refer to extracellular matrix compositions that are at least 90% decellularized such that the extracellular matrix composition is at least 90% without cells and/or cellular remnants. In other exemplary aspects described herein, the term "acellular" can refer to extracellular matrix compositions that are at least 95% decellularized such that the extracellular matrix composition is at least 95% without cells and/or cellular remnants. In other exemplary aspects described herein, the term "acellular" can refer to extracellular matrix compositions that are at least 96% decellularized such that the extracellular matrix composition is at least 96% without cells and/or cellular remnants. In still other exemplary aspects described herein, the term "acellular" can refer to extracellular matrix compositions that are at least 97% decellularized such that the extracellular matrix composition is at least 97% without cells and/or cellular remnants. In further exemplary aspects described herein, the term "acellular" can refer to extracellular matrix compositions that are at least 98% decellularized such that the extracellular matrix composition is at least 98% without cells and/or cellular remnants. In still further exemplary aspects described herein, the term "acellular" can refer to extracellular matrix compositions that are at least 99% decellularized such that the extracellular matrix composition is at least 99% without cells and/or cellular remnants. Thus, as used herein, the term "acellular" can refer to extracellular matrix compositions that are decellularized at levels of 80%, 81%, 82%, 83%, 84%, 85%, 86%, 87%, 88%, 89%, 90%, 91%, 92%, 93%, 94%, 95%, 96%, 97%, 98%, 99%, 100%, and any percentages falling between these values.

As used herein, the term "additive" refers to materials that can be selectively incorporated into the disclosed ECM materials to impart predetermined properties to the sterilized, acellular ECM compositions disclosed herein. Such additives can include, for example and without limitation, growth factors, cytokines, proteoglycans, glycosaminoglycans (GAGs), proteins, peptides, nucleic acids, small molecules, cells and pharmaceutical agents, such as statin drugs, corticosteroids, anti-arrhythmic drugs, nonsteroidal anti-inflammatory drugs, other anti-inflammatory compounds, nanoparticles, and metallic compounds.

As used herein, the term "contemporaneously" refers to the simultaneous and/or overlapping occurrence of events, as well as the sequential occurrence of events within thirty minutes before or after one another. Thus, if a first event occurs, then a second event can be said to have occurred contemporaneously with the first event if it occurred concurrently with the first event or within thirty minutes before or after the first event. For example, if a first method step is performed, then a second method step performed five minutes after the first method step can be said to be performed "contemporaneously" with the first method step. Similarly, if the second method step was performed ten minutes before performance of a third method step, then the second method step can be said to be performed "contemporaneously" with the third method step.

As used herein, the term "supercritical" refers to a fluid state of a material when it is held at or above its critical temperature and critical pressure. When a material is held at or above its critical temperature and critical pressure, then it typically adopts functional properties of both a gas and a liquid and is said to function as a supercritical fluid. Thus, for example, when carbon dioxide is held at or above its critical temperature (31.1° C.) and its critical pressure (1071 psi), it behaves as a supercritical carbon dioxide fluid and can, for example, exhibit the expansion properties of a gas while having the density of a liquid.

Figure 2:
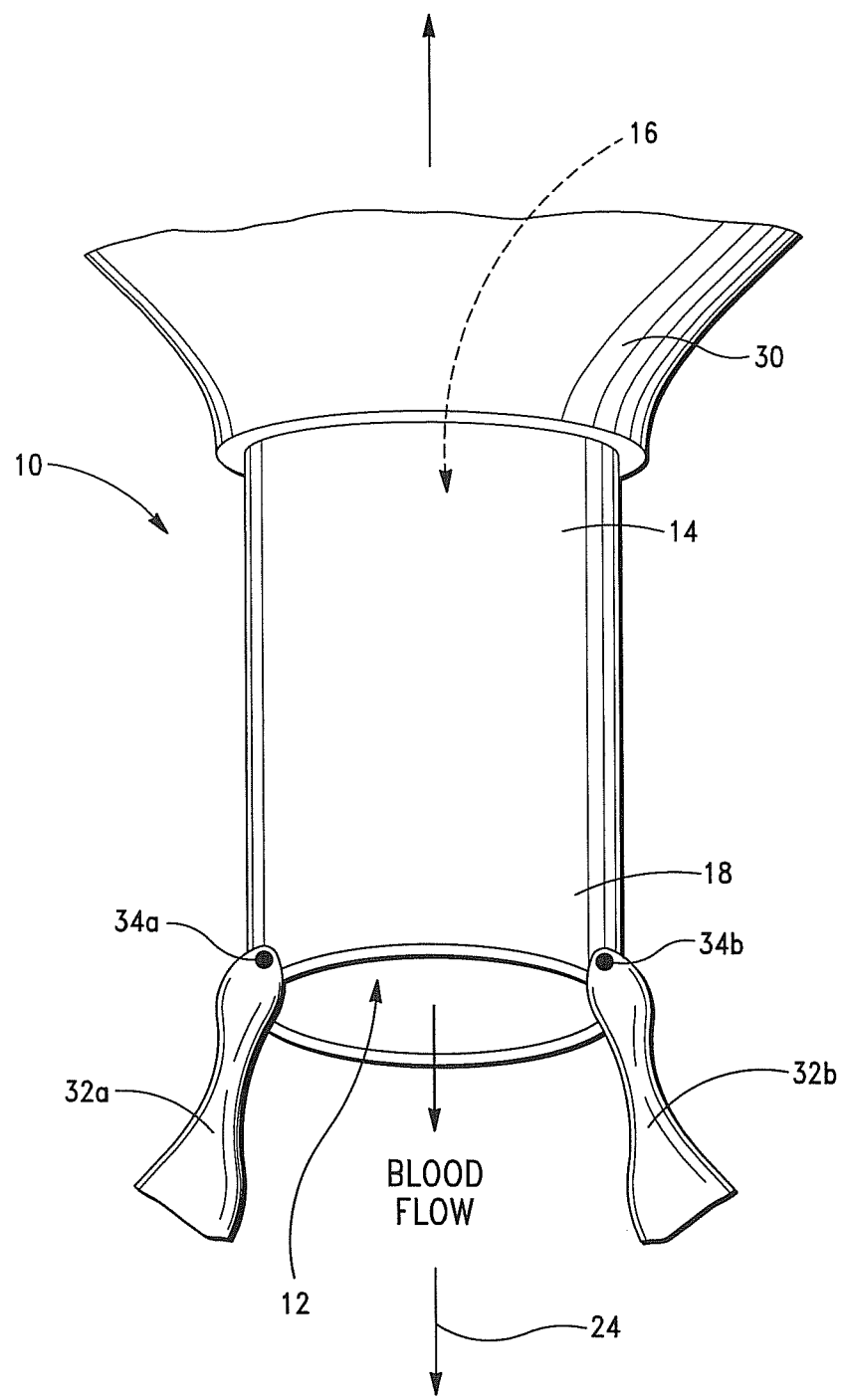
FIG. 2 is a perspective view of an ECM material conduit as it is attached to an annulus of an atrioventricular valve and to two papillary muscles, as described herein.
Figure 3:
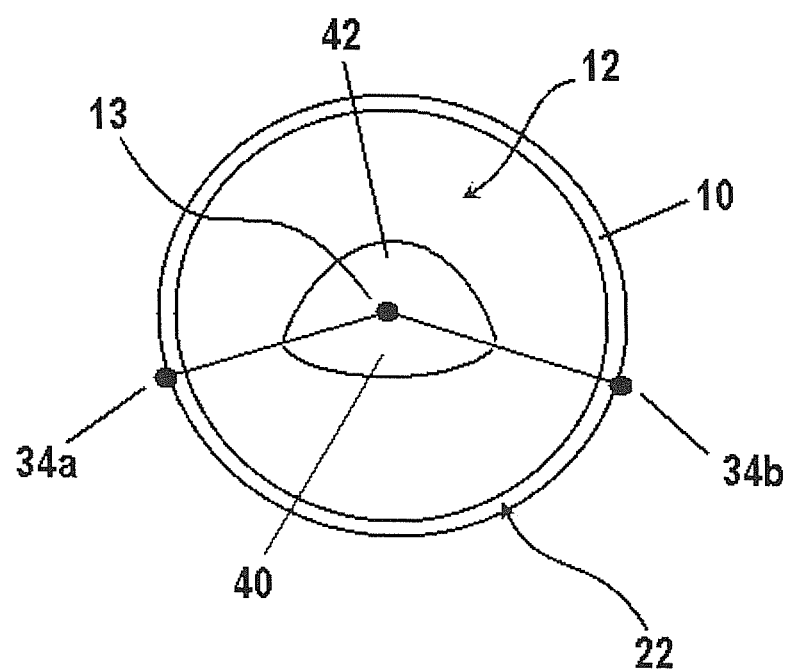
FIG. 3 is a bottom perspective view of the ECM material conduit shown in FIG. 2. The ECM material conduit depicted in FIG. 3 is attached to a first papillary muscle at a first attachment point and to a second papillary muscle at a second attachment point.

Described herein with reference to FIGS. 1-3 are methods of making and using extracellular matrix (ECM) material conduits. In one aspect, as depicted in FIGS. 2-3, an exemplary ECM material conduit 10 can define a lumen 12 and have an inlet portion 14 and an outlet portion 18. In this aspect, it is contemplated that the inlet portion 14 of the ECM material conduit 10 can comprise an inlet 16 of the lumen 12. It is further contemplated that the outlet portion 18 of the ECM material conduit 10 can comprise an outlet 20 of the lumen 12.

In additional aspects, the inlet portion 14 and the outlet portion 18 of an ECM material conduit 10 can each have an outer circumference. In one aspect, it is contemplated that the outer circumference of the outlet portion 18 of the ECM material conduit 10 can be substantially equal to the outer circumference of the inlet portion 14 of the ECM material conduit. Optionally, in this aspect, the ECM material conduit 10 can be substantially cylindrical. In another aspect, it is contemplated that the outer circumference of the outlet portion 18 of the ECM material conduit 10 can be greater than the outer circumference of the inlet portion 14 of the ECM material conduit. Optionally, in this aspect, the ECM material conduit 10 can be substantially frusto-conical. In a further aspect, it is contemplated that the outer circumference of the outlet portion 18 of the ECM material conduit 10 can be less than the outer circumference of the inlet portion 14 of the ECM material conduit. Optionally, in this aspect, the ECM material conduit 10 can be substantially frusto-conical.

In one aspect, it is contemplated that the ECM material conduit can have a longitudinal axis 24 and a longitudinal length ranging from about 10 mm to about 50 mm. In another aspect, it is contemplated that the outer circumferences of the inlet portion 14 and the outlet portion 18 of the ECM material conduit 10 can each range from about 25 mm to about 190 mm. Thus, it is further contemplated that, at the inlet portion 14 and the outlet portion 18 of the ECM material conduit 10, the lumen 12 of the ECM material conduit can have a diameter ranging from about 8 mm to about 60 mm. In an additional aspect, the ECM material conduit 10 can have a wall 22 having a thickness. In this aspect, it is contemplated that the thickness of the wall 22 of the ECM material conduit 10 can range from about 0.05 mm to about 3.00 mm.

In one exemplary aspect, the outlet portion 18 of the ECM material conduit 10 can comprise one or more extension portions that protrude outwardly from the ECM material conduit 10. It is contemplated that the extension portions can be configured to provide an attachment configuration for the papillary muscles that more closely mimics native functionality. It is further contemplated that the extension portions can be configured to promote fusion between the native papillary muscles attached to the ECM material conduit 10 and the regenerated AV valve formed following implantation of the ECM material conduit as described herein.

In exemplary aspects, when the outlet portion 18 of the ECM material conduit 10 comprises at least one extension portion as described herein, it is contemplated that one or more of the first, second, and third attachment points can be positioned on a corresponding extension portion of the at least one extension portion. In these aspects, it is contemplated that the at least one extension portion can comprise three extension portions, with each of the first, second, and third attachment points being positioned on a respective extension portion.

In exemplary aspects, a disclosed ECM material conduit can comprise any known ECM component or material, including, for example and without limitation, mucosal layers and components, submucosal layers and components, muscularis layers and components, and/or basement membrane layers and components. It is contemplated that a disclosed ECM material conduit can comprise an ECM material obtained from any mammalian tissue source, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. It is further contemplated that a disclosed ECM material conduit can comprise an ECM material obtained from ECM components or materials of one or more mammals including, for example and without limitation, humans, cows, pigs, dogs, sheep, cats, horses, rodents, and the like. Thus, it is contemplated that a disclosed ECM material conduit can comprise ECM components or materials from two or more of the same mammalian species, such as, for example and without limitation, two or more cows, two or more pigs, two or more dogs, or two or more sheep. It is further contemplated that a disclosed ECM material conduit can comprise ECM components or materials from two or more different mammalian species, such as, for example and without limitation, a pig and a cow, a pig and a dog, a pig and a sheep, or a cow and a sheep. It is still further contemplated that a disclosed ECM material conduit can comprise ECM components or materials obtained from a first tissue source, such as, for example and without limitation, SIS, from a first mammal, as well as ECM components or materials obtained from a second tissue source, such as, for example and without limitation, SS, from a second mammal.

In various aspects, a disclosed ECM material conduit 10 can be formed from a substantially flat sheet of ECM material. In these aspects, the ECM material conduit 10 can be formed by securing a first edge of the sheet of ECM material to a second, opposed edge of the sheet of ECM material such that a lumen 12 of the ECM material conduit is defined. It is contemplated that the first edge of the sheet of ECM material can be secured to the second edge of the sheet of ECM material using any conventional surgical attachment means, including, for example and without limitation, non-absorbable sutures, absorbable sutures, surgical pastes, surgical glues, staples, and the like. In one exemplary aspect, when non-absorbable sutures are used to secure the first edge of the sheet of ECM material to the second, opposed edge of the sheet of ECM material, it is contemplated that the non-absorbable sutures can be positioned on an outer surface of the ECM material conduit, thereby reducing the portion of the sutures positioned within the lumen of the ECM material conduit. In one optional aspect, it is contemplated that the second edge of the sheet of ECM material can be secured in overlapping relation with the first edge of the sheet of ECM material. In this aspect, it is further contemplated that the portion of the ECM material conduit 10 at which the first and second edges of the sheet overlap can be everted relative to the lumen of the ECM material conduit. In another optional aspect, it is contemplated that the second edge of the sheet of ECM material can be secured in substantial alignment with the first edge of the sheet of ECM material.

In additional aspects, a disclosed ECM material conduit 10 can comprise at least a portion of an intact, lumenal ECM material, such as, for example and without limitation, a lumenal portion of a native SIS layer. In these aspects, the intact ECM material defines a lumen.

In further aspects, a disclosed ECM material conduit 10 can be formed by growing cells, such as, for example and without limitation, fibroblasts, on an outer surface of a cylindrical mandrel using known in vitro methods. In these aspects, it is contemplated that the growth of cells on the outer surface of the mandrel can lead to production of one or more ECM materials. It is further contemplated that the ECM material conduit 10 can be decellularized using known methods or as disclosed herein.

In an additional aspect, a disclosed ECM material conduit 10 can be lyophilized using known methods. In a further aspect, when a disclosed ECM material conduit 10 has been lyophilized, it is contemplated that the ECM material conduit can be hydrated using known methods. In this aspect, it is contemplated that the lyophilized ECM material conduit can be hydrated in sterile water, saline solution, or a balanced salt solution for a period ranging from about 5 minutes to about 30 minutes.

Optionally, a disclosed ECM material conduit 10 can be a multi-layer construction of two or more layers of ECM material. In one exemplary aspect, a multi-layer ECM material conduit 10 can be formed from a luminal portion of an intact ECM. As used herein, the term "luminal" refers to a portion of a material that defines a lumen. In this aspect, the intact luminal ECM can have a first end and a second end and can define a lumen. Optionally, the first end of the intact ECM can be inverted into the lumen until it reaches the second end, thereby creating a multi-layer ECM material conduit. Alternatively, the first end of the intact SIS can be everted over itself until it reaches the second end, thereby creating a multi-layer ECM material conduit. In a further aspect, the multi-layer ECM material conduit can be lyophilized using known techniques, thereby creating a multi-laminate ECM material conduit. In one optional aspect, the multi-layer ECM material conduit can be positioned over a mandrel during lyophilization. In an alternative, optional aspect, during lyophilization of the multi-layer ECM material conduit, a cryoballoon can be positioned within the lumen of the multi-layer ECM material conduit and then inflated to press together the layers of the multi-layer ECM material conduit. It is further contemplated that any conventional lamination method can be used to laminate the layers of a multi-layer ECM material conduit together, thereby forming a multi-laminate ECM material conduit.

In one aspect, a disclosed ECM material conduit 10 can comprise a sterile, acellular ECM composition. In exemplary aspects, such a sterile, acellular ECM composition can be formed by contemporaneously sterilizing and decellularizing an isolated ECM material. More particularly, as disclosed in the following methods, desired sterilization and decellularization of the isolated ECM material can occur contemporaneously such that the native properties of the tissue composition are maintained and the ECM material is rendered sterile and acellular.

In exemplary aspects, the ECM material conduit 10 can have a multi-layer structure proximate the inlet and/or outlet portion of the ECM material conduit. In these aspects, it is contemplated that at least one end of the ECM material conduit can be everted or inverted along a portion of the length of the ECM material conduit to thereby form a multi-layer structure proximate the inlet and/or outlet portion of the ECM material conduit. It is further contemplated that the multi-layer structure can effectively act as a sewing ring for the ECM material conduit.

Sterilization and Decellularization of ECM Compositions for Use in ECM Material Conduits As described herein, the disclosed methods make use of rapid depressurization of an isolated ECM material to decellularize the ECM material such that it is acellular. This rapid depressurization of the ECM material occurs at depressurization rates that are significantly higher than the depressurization rates applied in previously known methods. In addition to decellularizing the ECM material as described herein, the rapid depressurization of the ECM material also can be used to incorporate desired sterilants and additives into the ECM material.

Optionally, it is contemplated that the ECM material of a disclosed ECM valve conduit can be sterilized using a known sterilization system, such as, for example and without limitation, the system described in U.S. Pat. No. 7,108,832, assigned to NovaSterilis, Inc., which patent is expressly incorporated herein by reference in its entirety. Thus, in some aspects, the system used to perform the disclosed methods can comprise a standard compressed storage cylinder and a standard air compressor used in operative association with a booster (e.g., a Haskel Booster AGT 7/30). In other aspects, the air compressor and booster can be replaced with a single compressor. In exemplary aspects, the compressed storage cylinder can be configured to receive carbon dioxide, and the booster can be a carbon dioxide booster.

The system can further comprise an inlet port, which allows one or more additives contained in a reservoir to be added to a reactor vessel through a valve and an additive line. As used herein, the term "reactor vessel" refers to any container having an interior space that is configured to receive an ECM material and permit exposure of the ECM material to one or more sterilants and additives, as disclosed herein. In exemplary aspects, the reactor vessel can be, without limitation, a basket, a bucket, a barrel, a box, a pouch, and other known containers. In one aspect, it is contemplated that the reactor vessel can be a syringe that is filled with an ECM material.

It is contemplated that a selected primary sterilant, such as, for example and without limitation, carbon dioxide, can be introduced to the reactor vessel from a header line via a valve and a supply line. It is further contemplated that a filter, such as, for example and without limitation, a 0.5 µm filter, can be provided in the supply line to prevent escape of material from the vessel. In exemplary aspects, a pressure gauge can be provided downstream of a shut-off valve in the header line to allow the pressure to be visually monitored. A check valve can be provided in the header line upstream of the valve to prevent reverse fluid flow into the booster. In order to prevent an overpressure condition existing in the header line, a pressure relief valve can optionally be provided.

In one aspect, depressurization of the reactor vessel can be accomplished using an outlet line and a valve in communication with the reactor vessel. In this aspect, it is contemplated that the depressurized fluid can exit the vessel via the supply line, be filtered by a filter unit, and then be directed to a separator, where filtered fluid, such as carbon dioxide, can be exhausted via an exhaust line. It is further contemplated that valves can be incorporated into the various lines of the apparatus to permit fluid isolation of upstream components.

In one exemplary aspect, the reactor vessel can comprise stainless steel, such as, for example and without limitation, 316 gauge stainless steel. In another exemplary aspect, the reactor vessel can have a total internal volume sufficient to accommodate the materials being sterilized, either on a laboratory or commercial scale. For example, it is contemplated that the reactor vessel can have a length of about 8 inches, an inner diameter of about 2.5 inches, and an internal volume of about 600 mL. In additional aspects, the reactor vessel can comprise a vibrator, a temperature control unit, and a mechanical stirring system comprising an impeller and a magnetic driver. In one optional aspect, it is contemplated that the reactor vessel can contain a basket comprising 316 gauge stainless steel. In this aspect, it is contemplated that the basket can be configured to hold materials to be sterilized while also protecting the impeller and directing the primary sterilant in a predetermined manner.

It is contemplated that the reactor vessel can be operated at a constant pressure or under continual pressurization and depressurization (pressure cycling) conditions without material losses due to splashing or turbulence, and without contamination of pressure lines via back-diffusion. It is further contemplated that the valves within the system can permit easy isolation and removal of the reactor vessel from the other components of the system. In one aspect, the top of the reactor vessel can be removed when depressurized to allow access to the interior space of the reactor vessel.

Optionally, the system can comprise a temperature control unit that permits a user to adjustably control the temperature within the reactor vessel.

In use, the disclosed apparatus can be employed in a method of producing a sterilized, acellular ECM composition, such as disclosed herein. However, it is understood that the disclosed apparatus is merely exemplary, and that any apparatus capable of performing the disclosed method steps can be employed to produce the sterilized, acellular ECM composition. Thus, the claimed method is in no way limited to a particular apparatus.

It is contemplated that significant reductions in colony-forming units (CFUs) can be achieved in accordance with the disclosed methods by subjecting an isolated ECM material to sterilization temperature and pressure conditions using a primary sterilant. Optionally, it is contemplated that the primary sterilant can be combined with one or more secondary sterilants to achieve desired sterilization. Optionally, it is further contemplated that selected additives can be incorporated into an ECM material to impart desired characteristics to the resulting ECM composition. It is still further contemplated that the disclosed methods can be employed to produce sterilized, acellular ECM compositions for implantation within the body of a subject.

As described herein, the disclosed methods make use of rapid depressurization of an isolated ECM material to render the ECM material acellular. This rapid depressurization of the ECM material occurs at depressurization rates that are significantly higher than the depressurization rates applied in previously known methods. In addition to rendering acellular the ECM material as described herein, the rapid depressurization of the ECM material also can be used to enhance the incorporation of desired sterilants and additives into the ECM material. Further, it is contemplated that the rapid depressurization of the ECM material can render the ECM material acellular while also improving retention of native growth factors, as compared to previously known decellularization methods. Still further, it is contemplated that the rapid depressurization of the ECM material can be used to improve retention of the tensile strength of the ECM material, as compared to previously known decellularization methods.

The disclosed methods not only do not significantly weaken the mechanical strength and bioptric properties of the ECM compositions, but also the methods are more effective in decellularizing the ECM compositions and in enhancing the incorporation of various additives into the ECM compositions. Thus, the disclosed sterilization and decellularization methods provide ECM compositions that are more decellularized and have a greater capacity to incorporate and then deliver more additives than ECM compositions known in the art. Moreover, the disclosed sterilization and decellularization methods provide ECM compositions that have greater amounts and/or concentrations of retained native growth factors and that have greater tensile strength than sterilized and decellularized ECM compositions known in the art.

In exemplary aspects, the primary sterilant can be carbon dioxide at or near its supercritical pressure and temperature conditions. However, it is contemplated that any conventional sterilant, including, for example, gas, liquid, or powder sterilants that will not interfere with the native properties of the ECM material, can be used as the primary sterilant.

In one exemplary aspect, the disclosed sterilization process can be practiced using carbon dioxide as a primary sterilant at pressures ranging from about 1000 to about 3500 psi and at temperatures ranging from about 25° C. to about 60° C. More preferably, when supercritical carbon dioxide is used, it is contemplated that the sterilization process can use carbon dioxide as a primary sterilant at pressures at or above 1071 psi and at temperatures at or above 31.1° C. In this aspect, the ECM material to be sterilized can be subjected to carbon dioxide at or near such pressure and temperature conditions for times ranging from about 10 minutes to about 24 hours, more preferably from about 15 minutes to about 18 hours, and most preferably, from about 20 minutes to about 12 hours. Preferably, the carbon dioxide employed in the disclosed systems and methods can be pure or, alternatively, contain only trace amounts of other gases that do not impair the sterilization properties of the carbon dioxide. For ease of further discussion below, the term "supercritical carbon dioxide" will be used, but it will be understood that such a term is non-limiting in that carbon dioxide within the pressure and temperature ranges as noted above can be employed satisfactorily in the practice of the disclosed methods. Within the disclosed pressure and temperature ranges, it is contemplated that the carbon dioxide can be presented to the ECM material in a gas, liquid, fluid or plasma form.

The secondary sterilants employed in the disclosed methods can, in some aspects, include chemical sterilants, such as, for example and without limitation, peroxides and/or carboxylic acids. Preferred carboxylic acids include alkanecarboxylic acids and/or alkanepercarboxylic acids, each of which can optionally be substituted at the alpha carbon with one or more electron-withdrawing substituents, such as halogen, oxygen and nitrogen groups. Exemplary species of chemical sterilants employed in the practice of the disclosed methods include, for example and without limitation, hydrogen peroxide ($H_2O_2$), acetic acid (AcA), peracetic acid (PAA), trifluoroacetic acid (TFA), and mixtures thereof. In one exemplary aspect, the chemical sterilants can include Sporeclenz® sterilant, which is a mixture comprising acetic acid, hydrogen peroxide, and peracetic acid.

It is contemplated that the secondary sterilants can be employed in a sterilization-enhancing effective amount of at least about 0.001 vol. % and greater, based on the total volume of the primary sterilant. It is further contemplated that the amount of secondary sterilant can be dependent upon the particular secondary sterilant that is employed. Thus, for example, it is contemplated that peracetic acid can be present in relatively small amounts of about 0.005 vol. % and greater, while acetic acid can be employed in amounts of about 1.0 vol. % and greater. Thus, it is contemplated that the concentration of the secondary sterilants can range from about 0.001 vol. % to about 2.0 vol. % and can typically be used as disclosed herein to achieve a sterilization-enhancing effect in combination with the disclosed primary sterilants, such as, for example and without limitation, supercritical carbon dioxide.

In one aspect, the method of producing a sterilized, acellular ECM composition can comprise harvesting a selected tissue from a mammal and rinsing the selected tissue in sterile saline or other biocompatible liquid, including, for example and without limitation, Ringer's solution or a balanced biological salt solution. In this aspect, the selected tissue can be, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium, epicardium, endocardium, myocardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In another aspect, the method can comprise freezing the selected tissue for a period ranging from about 12 to about 36 hours, more preferably, from about 18 to about 30 hours, and most preferably, from about 22 to about 26 hours. For example, it is contemplated that the period during which the selected tissue is frozen can be 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, and any other period of time falling between the preceding values. In an additional aspect, the method can comprise thawing the selected tissue in cold hypotonic tris buffer. Optionally, in this aspect, the method can comprise thawing the selected tissue in cold hypotonic tris buffer on ice with 5 mM ethylenediaminetetraacetic acid (EDTA). In exemplary aspects, it is contemplated that the steps of freezing and thawing the selected tissue can be cyclically repeated up to six times.

In another aspect, the method can comprise isolating an ECM material from the selected tissue. In this aspect, the ECM material can be any material comprising known extracellular matrix components, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium, epicardium, endocardium, myocardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone, and the like. In one exemplary, non-limiting aspect, the step of isolating an ECM material can comprise isolating SIS from a mammalian tissue source. In this aspect, the method can comprise: incising a wall of a small intestine along a path that is substantially parallel to the longitudinal axis of the small intestine; opening the small intestine along the path of the incision such that the small intestine lies flat on a surface; rinsing the small intestine with sterile saline or other biocompatible fluid; mechanically stripping the SIS of the small intestine from the surrounding smooth muscle and serosal layers and from the tunica mucosa, leaving essentially the submucosal and basement membrane layers. However, it is contemplated that the ECM material can be isolated using any conventional technique, including those described in: U.S. Pat. No. 4,902,508; U.S. Pat. No. 5,275,826; U.S. Pat. No. 5,281,422; U.S. Pat. No. 5,554,389; U.S. Pat. No. 6,579,538; U.S. Pat. No. 6,933,326; U.S. Pat. No. 7,033,611; Voytik-Harbin et al., "Identification of Extractable Growth Factors from Small Intestinal Submucosa," *J. Cell. Biochem.*, vol. 67, pp. 478-491 (1997); Hodde et al., "Virus Safety of a Porcine-Derived Medical Device: Evaluation of a Viral Inactivation Method," *Biotech. & Bioeng.*, vol. 79, No. 2, pp. 211-216 (2001); Badylak et al., "The Extracellular Matrix as a Scaffold for Tissue Reconstruction," *Cell & Developmental Biology*, vol. 13, pp. 377-383 (2002); Robinson et al., "Extracelular Matrix Scaffold for Cardiac Repair," *Circulation*, vol. 112, pp. I-135-I-143 (2005); Hodde et al., "Effects of Sterilization on an Extracellular Matrix Scaffold: Part I. Composition and Matrix Architecture," *J. Mater. Sci.: Mater. Med.*, vol. 18, pp. 537-543 (2007); and Hodde et al., "Effects of Sterilization on an Extracellular Matrix Scaffold: Part II. Bioactivity and Matrix Interaction," *J. Mater. Sci.: Mater. Med.*, vol. 18, pp. 545-550 (2007), each of which is expressly incorporated herein by reference in its entirety.

In an additional aspect, the method can comprise incubating the isolated ECM material for 24 to 48 hours in 0.5-1% Triton X-100/0.5-1% Deoxycholic acid with 5 mM EDTA in Dulbecco's Phosphate Buffered Saline (DPBS) (Lonza Walkersville, Inc.). In this aspect, it is contemplated that flat or sheet-like ECM materials, such as stomach submucosa (SS), small intestinal submucosa (SIS), and bladder submucosa (UBS), can be incubated in a stretched configuration. It is further contemplated that ECM material conduits or other lumenal ECM materials, such as ureters, arteries, veins, and tubular SIS, can be perfused with the various disclosed solutions through soaking and by use of a peristaltic pump.

In a further aspect, after incubation, the method can comprise rinsing the ECM material with DPBS. In this aspect, it is contemplated that the step of rinsing the ECM material can comprise rinsing the ECM material up to six times, including one, two, three, four, five, or six times, with each rinse lasting for about thirty minutes. In an exemplary aspect, it is contemplated that the step of rinsing the ECM material can comprise rinsing the ECM material three times, with each rinse lasting for about thirty minutes.

Optionally, in exemplary aspects, the method can further comprise a second incubation procedure. In these aspects, the second incubation procedure can comprise incubating the ECM material in isotonic tris buffer containing 10-50 µg/mL of RNAase/0.2-0.5 µg/mL DNAase with 5 mM EDTA. It is contemplated that the step of incubating the ECM material in isotonic tris buffer can be performed at a temperature of about 37° C., substantially corresponding to the temperature of a human body. It is further contemplated that the step of incubating the ECM material in isotonic tris buffer can be performed for a period ranging from about 30 minutes to about 24 hours, more preferably, from about 1 hour to about 18 hours, and most preferably, from about 2 hours to about 12 hours. In an additional aspect, the second incubation procedure can further comprise rinsing the ECM material with DPBS. In this aspect, it is contemplated that the step of rinsing the ECM material can comprise rinsing the ECM material three times, with each rinse lasting for about thirty minutes.

In yet another aspect, whether or not the second incubation procedure is performed, the method can comprise storing the ECM material at a temperature ranging from about 1° C. to about 10° C., more preferably, from about 2° C. to about 6° C., and, most preferably, from about 3° C. to about 5° C. In an exemplary aspect, the ECM material can be stored at 4° C.

In an additional aspect, the method can comprise introducing the ECM material into the interior space of the reactor vessel. Optionally, in this aspect, one or more secondary sterilants from the reservoir can be added into the interior space of the reactor vessel along with the ECM material. In these aspects, it is contemplated that the one or more secondary sterilants from the reservoir can be added into the interior space of the reactor vessel before, after, or contemporaneously with the ECM material. It is further contemplated that the temperature control unit can be selectively adjusted to produce a desired temperature within the interior space of the reactor vessel. In a further aspect, the method can comprise equilibrating the pressure within the reactor vessel and the pressure within the storage cylinder. For example, in this aspect, it is contemplated that the pressure within the reactor vessel and the pressure within the storage cylinder can be substantially equal to atmospheric pressure. In yet another aspect, after equilibration of the pressures within the apparatus, the method can comprise operating the magnetic driver to activate the impeller of the reactor vessel. In still a further aspect, the method can comprise selectively introducing the primary sterilant from the storage cylinder into the reactor vessel until a desired pressure within the reactor vessel is achieved. In this aspect, it is contemplated that the step of selectively introducing the primary sterilant into the reactor vessel can comprise selectively activating the air compressor and the booster to increase flow of the primary sterilant into the reactor vessel. In exemplary aspects, the air compressor and booster can be activated to subject the ECM material to supercritical pressures and temperatures, such as, for example and without limitation, the pressures and temperatures necessary to produce supercritical carbon dioxide, for a time period ranging from about 20 minutes to about 60 minutes.

In a further aspect, the method can comprise rapidly depressurizing the reactor vessel. In this aspect, a predetermined amount of primary sterilant, such as, for example and without limitation, supercritical carbon dioxide, can be released from the reactor vessel through the depressurization line. It is contemplated that the primary sterilant can be released from the reactor vessel through opening of the valve coupled to the reactor vessel to thereby rapidly reduce the pressure within the reactor vessel. As used herein, the term "rapid depressurization" refers to depressurization of the reactor vessel at a rate greater than or equal to 400 psi/min. For example, it is contemplated that the reactor vessel can be rapidly depressurized at a depressurization rate ranging from about 2.9 MPa/min. to about 18.0 MPa/min. (about 400 psi/min. to about 2,600 psi/min.), more preferably, from about 5.0 MPa/min. to about 10.0 MPa/min. (700 psi/min. to about 1500 psi/min.), and, most preferably, from about 7.0 MPa/min. to about 8.0 MPa/min. (about 1000 psi/min. to about 1200 psi/min.). Thus, these rapid depressurizations are significantly greater than the 300 psi/min. depressurization rate disclosed in U.S. Pat. No. 7,108,832. Without being bound by any particular theory, it is believed that the disclosed rapid depressurization rates increase the level of decellularization achieved in the ECM material. For example, it is contemplated that the rapid depressurization of a disclosed ECM material can lead to levels of decellularization in the ECM material of greater than about 96%, including 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, and 100%.

In exemplary aspects, the method can further comprise the step of incorporating one or more additives into the ECM material. In these aspects, it is contemplated that the one or more additives can be provided in either a powder or a liquid form. In one optional aspect, the step of incorporating the one or more additives can comprise introducing the one or more additives into the reactor vessel during the step of rapidly depressurizing the reactor vessel. In this aspect, it is contemplated that the introduction of the one or more additives can be characterized as a conventional foaming process. In another optional aspect, the step of incorporating the one or more additives can comprise introducing the one or more additives into the reactor vessel after the step of rapidly depressurizing the reactor vessel. In this aspect, it is contemplated that the one or more additives can be added to the ECM material after the rapid depressurization of the reactor vessel has caused the ECM material to swell and/or expand, thereby permitting improved penetration of the additives into the ECM material. It is further contemplated that, in an exemplary aspect, the one or more additives can be added to the ECM material within about thirty minutes after the rapid depressurization of the reactor vessel. In a further optional aspect, the step of incorporating the one or more additives can comprise introducing the one or more additives into the reactor vessel both during and after the step of rapidly depressurizing the reactor vessel. In this aspect, it is contemplated that the one or more additives can be released into the reactor vessel in both a quick manner and a slow, extended manner. In still a further optional aspect, the step of incorporating the one or more additives can comprise introducing the one or more additives into the reactor vessel before the step of rapidly depressurizing the reactor vessel.

The disclosed additives can be incorporated into the ECM material to impart selected properties to the resulting sterilized, acellular ECM composition. Thus, it is contemplated that the one or more additives can be selected to replace or supplement components of the ECM material that are lost during processing of the ECM material as described herein. For example, and as described below, the one or more additives can comprise growth factors, cytokines, proteoglycans, glycosaminoglycans (GAGs), proteins, peptides, nucleic acids, small molecules, drugs, or cells. It is further contemplated that the one or more additives can be selected to incorporate non-native components into the ECM material. For example, the one or more additives can comprise, for example and without limitation, growth factors for recruiting stem cells, angiogenic cytokines, and anti-inflammatory cytokines. It is still further contemplated that the one or more additives can be pharmaceutical agents, such as statins, corticosteroids, non-steroidal anti-inflammatory drugs, anti-inflammatory compounds, anti-anhythmic agents, and the like. It is still further contemplated that the one or more additives can be nanoparticles, such as, for example and without limitation, silver nanoparticles, gold nanoparticles, platinum nanoparticles, iridium nanoparticles, rhodium nanoparticles, palladium nanoparticles, copper nanoparticles, zinc nanoparticles, and other metallic nanoparticles. It is still further contemplated that the one or more additives can be metallic compounds. In one exemplary aspect, the one or more additives can be selected to pharmaceutically suppress the immune response of a subject following implantation of the resulting ECM composition into the body of a subject.

In one aspect, the one or more additives can comprise one or more growth factors, including, for example and without limitation, transforming growth factor-β 1, 2, or 3 (TGF β 1, 2, or 3), fibroblast growth factor-2 (FGF-2), also known as basic fibroblast growth factor (bFGF), vascular endothelial growth factor (VEGF), placental growth factor (PGF), connective tissue growth factor (CTGF), hepatocyte growth factor (HGF), Insulin-like growth factor (IGF), macrophage colony stimulating factor (M-CSF), platelet derived growth factor (PDGF), epidermal growth factor (EGF), and transforming growth factor-α (TGF-α).

In another aspect, the one or more additives can comprise one or more cytokines, including, for example and without limitation, stem cell factor (SCF), stromal cell-derived factor-1 (SDF-1), granulocyte macrophage colony-stimulating factor (GM-CSF), interferon gamma (IFN-gamma), Interleukin-3, Interleukin-4, Interleukin-10, Interleukin-13, Leukemia inhibitory factor (LIF), amphiregulin, thrombospondin 1, thrombospondin 2, thrombospondin 3, thrombospondin 4, thrombospondin 5, and angiotensin converting enzyme (ACE).

In an additional aspect, the one or more additives can comprise one or more proteoglycans, including, for example and without limitation, heparan sulfate proteoglycans, betaglycan, syndecan, decorin, aggrecan, biglycan, fibromodulin, keratocan, lumican, epiphycan, perlecan, agrin, testican, syndecan, glypican, serglycin, selectin, lectican, versican, neurocan, and brevican.

In a further aspect, the one or more additives can comprise one or more glycosaminoglycans, including, for example and without limitation, heparan sulfate, hyaluronic acid, heparin, chondroitin sulfate B (dermatan sulfate), and chondroitin sulfate A.

In still a further aspect, the one or more additives can comprise one or more proteins, peptides, or nucleic acids, including, for example and without limitation, collagens, elastin, vitronectin, versican, laminin, fibronectin, fibrillin-1, fibrillin-2, plasminogen, small leucine-rich proteins, cell-surface associated protein, cell adhesion molecules (CAMs), a matrikine, a matrix metalloproteinase (MMP), a cadherin, an immunoglobin, a multiplexin, cytoplasmic domain-44 (CD-44), amyloid precursor protein, tenascin, nidogen/entactin, fibulin I, fibulin II, integrins, transmembrane molecules, and osteopontin.

In yet another aspect, the one or more additives can comprise one or more pharmaceutical agents, including, for example and without limitation, statin drugs, for example, cerevastatin, atorvastatin, fluvastatin, lovastatin, mevastatin, pitavastatin, pravastatin, rosuvastatin, and simvastatin, corticosteroids, non-steroidal anti-inflammatory drugs, anti-inflammatory compounds, anti-arrhythmic agents, antimicrobials, antibiotics, and the like.

In exemplary aspects, the steps of introducing the one or more additives into the reactor vessel can comprise opening the valve to allow the one or more additives to flow from the reservoir into the inlet port. Prior to pressurization, it is contemplated that the one or more additives can be introduced directly into the reactor vessel prior to sealing and/or via the inlet port.

It is contemplated that the disclosed rapid depressurization and repressurization of the reactor vessel, with or without the addition of the one or more additives, can be repeated for any desired number of cycles. It is further contemplated that the cycles of depressurization and repressurization, as well as the introduction of the primary sterilants and/or secondary sterilants and/or additives, can be automatically controlled via a controller that is configured to selectively open and/or close the various valves of the system to achieve desired pressure conditions and cycles.

In some aspects, the disclosed methods can further comprise the step of agitating the contents of the reactor vessel. In these aspects, it is contemplated that the step of agitating the contents of the reactor vessel can comprise periodically agitating the contents of the reactor vessel using a vibrator. It is further contemplated that the agitation of the reactor vessel can be intermittent, continual, or continuous. In exemplary aspects, the step of agitating the contents of the reactor vessel can occur during the step of introducing the primary sterilant into the reactor vessel. It is contemplated that the agitation of the contents of the reactor vessel can enhance the mass transfer of the sterilants and/or additives by eliminating voids in the fluids within the reactor vessel to provide for more complete contact between the ECM material and the sterilants and/or additives. It is further contemplated that the step of agitating the contents of the reactor vessel can comprise selectively adjusting the intensity and duration of agitation so as to optimize sterilization times, temperatures, and pressurization/depressurization cycles.

In a further aspect, after the sterilization and decellularization of the ECM material is complete, the method can further comprise depressurizing the reactor vessel and deactivating the magnetic drive so as to cease movement of the stirring impeller. Finally, the method can comprise the step of removing the resulting sterilized, acellular ECM composition through the top of the reactor vessel.

Methods of Regenerating Heart Valves Using the ECM Material Conduits

Also disclosed herein are methods of regenerating heart valves. In an exemplary aspect, a method of regenerating an atrioventricular (AV) valve to replace a defective AV valve within a heart of a subject is disclosed. In this aspect, and with reference to FIG. 1, it is contemplated that the defective AV valve is attached at an annulus between an atrium and a ventricle within the heart of the subject and is functionally coupled to a plurality of papillary muscles 32 within the ventricle of the heart of the subject. As used herein, the term "atrioventricular (AV) valve" can refer to either a mitral (bicuspid) valve or a tri-cuspid valve within the heart of the subject. It is contemplated that, if the defective AV valve is a mitral valve, then the defective AV valve is attached at an annulus between the left atrium and the left ventricle of the heart of the subject. It is further contemplated that, if the defective AV valve is a tri-cuspid valve, then the defective AV valve is attached at an annulus between the right atrium and the right ventricle of the heart of the subject.

In one aspect, and with reference to FIG. 2, a disclosed method of regenerating an AV valve can comprise removing the defective AV valve from the heart of the subject, thereby exposing an annular region 30 of the heart of the subject. As used herein, the term "annular region" refers to the portion of the heart of a subject that is proximate to the native position of an annulus between an atrium and a ventricle within the heart of the subject. When an annulus is positioned within the heart of the subject, the annular region 30 includes the annulus as well as the heart muscle proximate the annulus. When the annulus has been removed from the heart of the subject, the annular region 30 includes the heart muscle proximate the former position of the annulus within the heart of the subject.

In one optional aspect, it is contemplated that the annulus of the annular region 30 can be removed from the heart of the subject along with the defective AV valve. In another optional aspect, it is contemplated that the chordae tendineae that are coupled to the defective AV valve can be removed from the heart of the subject along with the defective AV valve. It is contemplated that the step of removing the defective AV valve can further comprise placing the subject on cardiopulmonary bypass. It is further contemplated that the step of removing the defective AV valve can further comprise arresting and/or fibrillating the heart of the subject and exposing the defective valve through an incision in an atrium of the heart of the subject.

In an additional aspect, a disclosed method of regenerating an AV valve can further comprise implanting an ECM material conduit 10, such as those disclosed herein. In this aspect, and as further disclosed herein, the ECM material conduit 10 can define a lumen 12 and have an inlet portion 14 and an outlet portion 18, with each of the inlet portion and the outlet portion having an outer circumference. It is contemplated that the lumen 12 defined by the ECM material conduit 10 can have a center point 13 proximate the outlet portion 18 of the ECM material conduit. In a further aspect, the step of implanting an ECM material conduit 10 can comprise securing the inlet portion 14 of the ECM material conduit to the annular region 30 and securing the outlet portion of the ECM material conduit to at least two of the plurality of papillary muscles 32. In this aspect, it is contemplated that, when the annulus is not removed from the heart of the subject, the inlet portion 14 of the ECM material conduit 10 can be secured to the annulus. It is further contemplated that, when the annulus is removed from the heart of the subject, the inlet portion 14 of the ECM material conduit 10 can be secured to heart muscle proximate the native location of the excised annulus. It is still further contemplated that the ECM material conduit 10 can be secured to the annular region 30 and/or the papillary muscles 32 using any conventional surgical attachment means, including, for example and without limitation, non-absorbable sutures, absorbable sutures, surgical pastes, surgical glues, staples, and the like. Optionally, in one aspect, the ECM material conduit 10 can be secured to the papillary muscles 32 before it is secured to the annular region. In this aspect, it is contemplated that, after the ECM material conduit 10 has been properly secured to the papillary muscles 32, the length of the ECM material conduit 10 along the longitudinal axis 24 can be trimmed as necessary to eliminate any excess length while retaining adequate tissue for proper attachment of the ECM material conduit to the annular region 30. Alternatively, in another aspect, the ECM material conduit 10 can be secured to the annular region 30 before it is secured to the papillary muscles 32. In this aspect, it is contemplated that, after the ECM material conduit 10 has been properly secured to the annular region 30, the length of the ECM material conduit along the longitudinal axis 24 can be trimmed as necessary to eliminate any excess length while retaining adequate tissue for proper attachment of the ECM material conduit to the papillary muscles 32.

Optionally, in one aspect, and with reference to FIGS. 2-3, the disclosed method can be used to regenerate a bi-cuspid AV valve within the heart of the subject. In this aspect, the step of implanting an ECM material conduit 10 can comprise securing the outlet portion 18 of the ECM material conduit to only two papillary muscles (i.e., only a first papillary muscle 32a and a second papillary muscle 32b) of the plurality of papillary muscles. As one will appreciate, the left ventricle only has two papillary muscles, whereas the right ventricle has three papillary muscles. Nonetheless, it is contemplated that, regardless of whether the defective AV valve is a mitral valve or a tri-cuspid valve, the replacement AV valve regenerated by the ECM material conduit will be a bi-cuspid valve. When the defective AV valve is a tri-cuspid valve, it is contemplated that the first papillary muscle 32a can be the anterior papillary muscle of the right ventricle and that the second papillary muscle 32b can be the posterior papillary muscle of the right ventricle. It is further contemplated that the first papillary muscle 32a can be the anterior papillary muscle of the right ventricle and that the second papillary muscle 32b can be the septal papillary muscle of the right ventricle. It is still further contemplated that the first papillary muscle 32a can be the posterior papillary muscle of the right ventricle and that the second papillary muscle 32b can be the septal papillary muscle of the right ventricle.

In a further aspect, the step of implanting an ECM material conduit can comprise securing the outlet portion of the ECM material conduit 10 to the first papillary muscle 32a at a first attachment point 34a and to a second papillary muscle 32b at a second attachment point 34b. In this aspect, it is contemplated that the second attachment point 34b can be spaced from the first attachment point 34a along the outer circumference of the outlet portion 18 of the ECM material conduit 10. In yet another aspect, and with reference to FIG. 3, it is contemplated that the center point 13 of the lumen 12 of the ECM material conduit 10 can correspond to a vertex of an angle 40 formed between the first attachment point 34a and the second attachment point 34b. In this aspect, it is further contemplated that the angle 40 formed between the first attachment point and the second attachment point can have a desired magnitude. In an exemplary aspect, the desired magnitude of the angle 40 formed between the first attachment point 34a and the second attachment point 34b can range from about 120° to about 150° C. In this aspect, and as shown in FIG. 3, it is contemplated that the angle 40 formed between the first attachment point 34a and the second attachment point 34b can have a complementary angle 42 within the lumen 12. It is further contemplated that the complementary angle 42 within the lumen 12 can have a magnitude ranging from about 210° to about 240° C.

In exemplary aspects, when the outlet portion 18 of the ECM material conduit 10 comprises at least one extension portion as described herein, it is contemplated that one or more of the first and second attachment points 34a, 34b can be positioned on a corresponding extension portion of the at least one extension portion. In these aspects, it is contemplated that the at least one extension portion can comprise two extension portions, with each of the first and second attachment points 34a, 34b being positioned on a respective extension portion.

Optionally, in another aspect, the disclosed method can be used to regenerate a tri-cuspid AV valve within the heart of the subject. In this aspect, when the defective valve is the tri-cuspid valve, the step of implanting an ECM material conduit 10 can comprise securing the outlet portion 18 of the ECM material conduit to each of the three papillary muscles within the right ventricle. In a further aspect, the step of implanting an ECM material conduit 10 can comprise securing the outlet portion 18 of the ECM material conduit to a first papillary muscle at a first attachment point, to a second papillary muscle at a second attachment point, and to a third papillary muscle at a third attachment point. In this aspect, it is contemplated that the first, second, and third attachment points can be spaced from one another along the outer circumference of the outlet portion of the ECM material conduit. In an exemplary aspect, it is contemplated that the first, second, and third attachment points can optionally be substantially equally spaced along the outer circumference of the outlet portion of the ECM material conduit. However, it is contemplated that the spacing of the first, second, and third attachment points can vary depending upon the native anatomy and positioning of the papillary muscles. It is contemplated that, in exemplary aspects, where the first, second, and third attachment points can be spaced such that 40% of the operative circumference of the ECM material conduit is between the septal and anterior papillary muscles, 30% of the circumference of the ECM material conduit is between the anterior and posterior papillary muscles, and 30% of the circumference of the ECM material conduit is between the posterior and septal papillary muscles. In exemplary aspects, when the outlet portion 18 of the ECM material conduit 10 comprises at least one extension portion as described herein, it is contemplated that one or more of the first, second, and third attachment points can be positioned on a corresponding extension portion of the at least one extension portion. In these aspects, it is contemplated that the at least one extension portion can comprise three extension portions, with each of the first, second, and third attachment points being positioned on a respective extension portion.

After the ECM material conduit 10 is properly secured to the annular region and to the papillary muscles, and after any necessary trimming or sculpting of the ECM material conduit has been completed, the atrium of the heart of the subject can be closed and the heart of the subject can be restarted.

It is contemplated that, following implantation of the ECM material conduit as disclosed herein, the ECM material conduit can become populated with cells from the subject that will gradually remodel the ECM material of the ECM material conduit into heart valve tissue that is identical or substantially identical to properly functioning native heart valve tissue. It is further contemplated that stem cells can migrate to the ECM material conduit from the points at which the ECM material conduit is attached to the papillary muscles and the annular region within the heart of the subject. It is still further contemplated that, during circulation of epithelial and endothelial progenitor cells, the surfaces of the ECM material conduit can rapidly become lined or covered with epithelial and/or endothelial progenitor cells. It is still further contemplated that the points at which the ECM material conduit is attached to the papillary muscles and the annular region can serve as points of constraint that direct the remodeling of the ECM material into leaflet tissue or chordae tendineae that are identical or substantially identical to properly functioning native leaflet tissue and properly functioning native chordae tendineae. It is still further contemplated that, where the annulus is removed from the annular region prior to attachment of the ECM material conduit, the inlet portion of the ECM material conduit can direct the remodeling of an annulus that is identical or substantially identical to a properly functioning native annulus.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in .degree. C. or is at ambient temperature, and pressure is at or near atmospheric.

Example One

Figure 4:
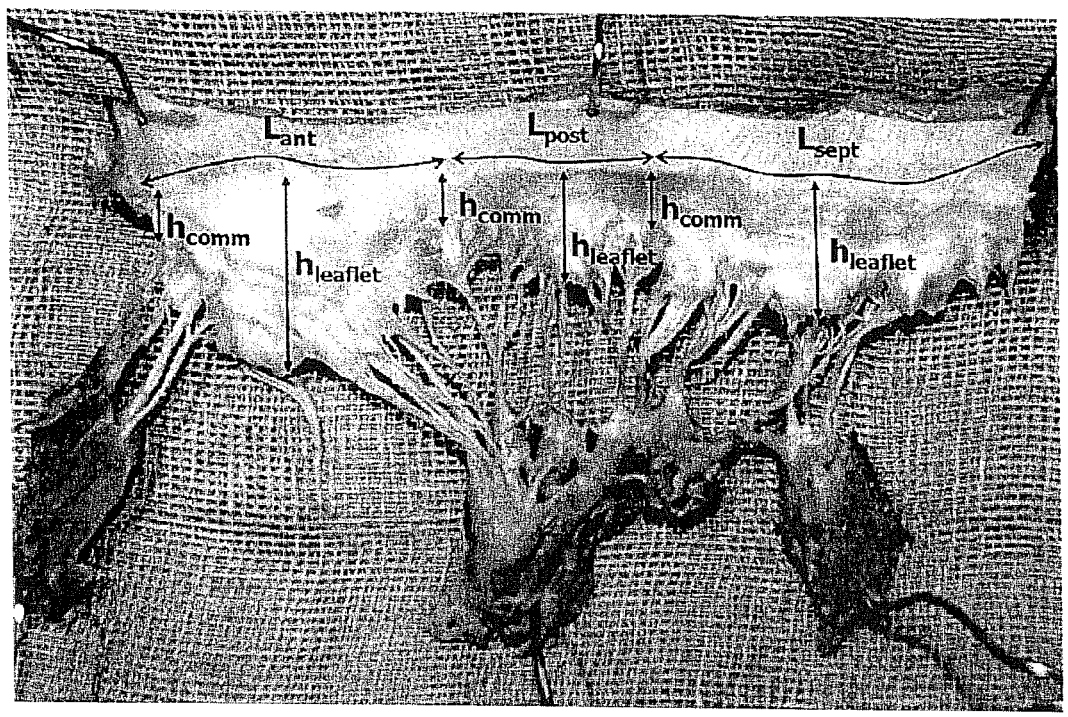
FIG. 4 is an image of a native tri-cuspid valve following removal from the heart of a subject.

Exemplary valve dimensions were measured for both porcine and human valves as shown in FIG. 4 and Table 1. These measurements supported the use of ECM material conduits having a 30 mm annular diameter and a length ranging from about 32-35 mm. These design criteria also suggested that the distal valve should be implanted so as to achieve 40% of the circumference between the septal and anterior papillary muscles, 30% between the anterior and posterior papillary muscles, and 30% between the posterior and septal papillary muscles.

TABLE 1

|  | Leaflet | Porcine | Human |
|---|---|---|---|
| Weight (g) |  | 376 ± 188 | 380 ± 180 |
| Annular length (mm) | Anterior | 46.57 ± 8.53 | 40.00 ± 6.71 |
|  | Septal | 39.15 ± 9.00 | 32.04 ± 5.71 |
|  | Posterior | 34.12 ± 7.55 | 28.94 ± 5.40 |
| Thickness (mm) | Anterior | 0.390 ± 0.102 | 0.396 ± 0.101 |
|  | Septal | 0.378 ± 0.106 | 0.380 ± 0.086 |
|  | Posterior | 0.379 ± 0.105 | 0.413 ± 0.079 |
| Commissure height (mm) | Anterior | 7.80 ± 2.02 | 11.16 ± 1.49* |
|  | Septal | 6.73 ± 1.58 | 13.36 ± 2.16* |
|  | Posterior | 6.69 ± 1.36 | 13.25 ± 2.22* |
| Leaflet maximum height (mm) | Anterior | 19.93 ± 3.53 | 24.96 ± 3.12* |
|  | Septal | 18.82 ± 3.22 | 21.54 ± 5.31 |
|  | Posterior | 18.62 ± 4.08 | 21.40 ± 2.69 |

Example Two

Figure 5:
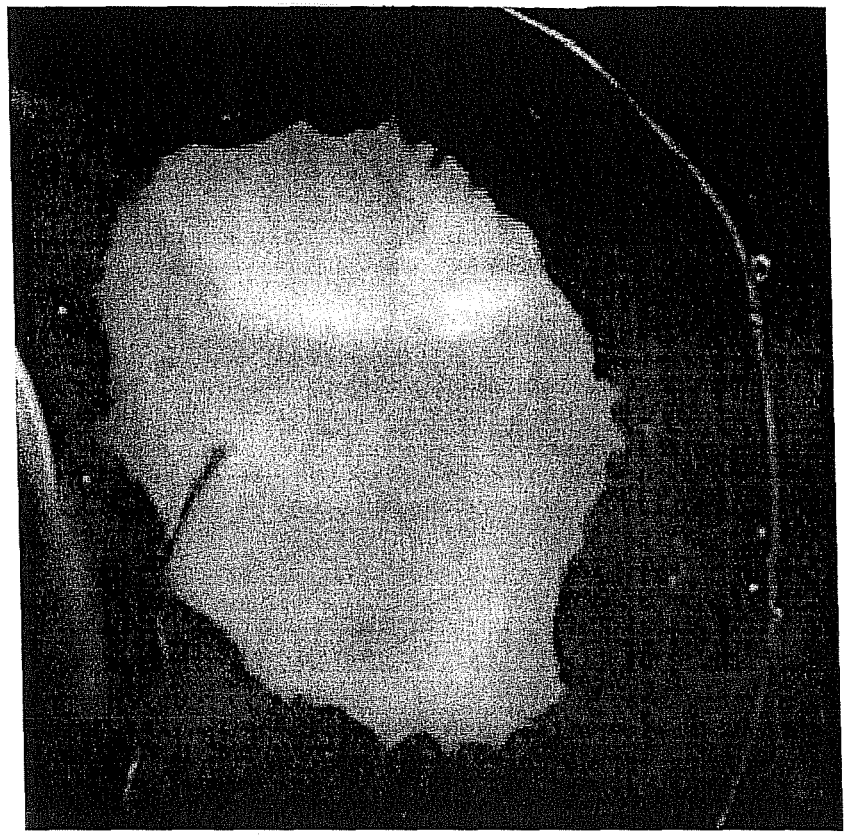
FIG. 5 is an image of an ECM material conduit following implantation of the ECM material conduit following removal of a native tri-cuspid valve.

In vitro hemodynamic evaluation of an exemplary ECM material conduit was achieved in a physiologic right heart simulator. These studies demonstrated that when a valve construct 30 mm diameter and 35 mm in length was implanted so that the papillary muscle attachment was performed so that 40% of the circumference was between the septal and anterior papillary muscles, 30% was between the anterior and posterior, and 30% was between the posterior and septal, the valve opened and closed with a low transvalvular pressure gradient and closing volume and no regurgitation. An image of the closed valve in the in vitro flow loop is shown in FIG. 5. These studies demonstrated that the valve was functional under physiologic conditions.

In vitro mechanical evaluation was also performed on the tricuspid valve seam (n=8) and the maximum tensile break force for the sewn seam was found to be 52.1±14.1 N (11.7±3.16 $lb_f$) with a minimum and maximum of 34.8 N (7.82 $lb_f$), and 72.3 N (16.25 $lb_f$), respectively. The tensile force, ball burst, and suture pull-out forces for the 4-ply ECM conduit was determined to be 19.35±5.51N (4.35±1.24 $lb_f$), 126.6±30.2 N (6699±1598 mmHg), and 11.12±2.08 N (2.50±0.47 $lb_f$), respectively. These values are more than adequate to meet the force requirements for this valve in the low-pressure environment of the right heart.

Example Three

In a non-GLP study using a sheep model, the tricuspid valve in four sheep was replaced by a 2-ply ECM valve conduit as described herein. The procedure was successfully completed on all four animals. All of the animals were euthanized on schedule at 3, 5, 8, and 12 months post-implant. Echocardiographic results (Table 2) for all four animals showed that the mobility and function of the leaflets appear normal, with only a mild level of backflow through the valve after closure. The valves were seen to experience normal forward flow with mild regurgitation. Necropsy results showed that the replacement valves appeared to be grossly within normal limits and at 12 months the leaflets remodeled and appear similar to native valve tissue.

TABLE 2

| Animal#/ Implant Date | Assessment Time Point (weeks) | Regurgitation | Comments |
|---|---|---|---|
| 2948 (Jan. 13, 2011) | 0 | Mild | Mobility and function of the leaflet appear normal. Leaflet coaptation looks sufficient and annulus appears morphologically normal. Normal forward flow with mild to trivial regurgitation. |
|  | 1 | Mild |  |
|  | 4 | Mild |  |
|  | 12 | Mild |  |
| 2981 (Feb. 14, 2011) | 0 | Mild | Mobility and function of the leaflets appears normal. Leaflet coaptation looks sufficient and annulus appears morphologically normal. Normal forward flow with a mild level of regurgitation. |
|  | 1 | Mild |  |
|  | 4 | Mild |  |
|  | 20 | Mild to Moderate |  |
| 2969 (Mar. 10, 2011) | 0 | Mild | Mobility and function of the leaflets appears normal. Leaflet coaptation looks sufficient and annulus appears morphologically normal. Normal forward flow with a mild to no regurgitation. |
|  | 20 | None |  |
|  | 24 | Mild |  |
|  | 32 | Mild |  |
| 2966 (Feb. 10, 2011) | 0 | None | Mobility and function of the leaflets appears normal. Leaflet coaptation looks sufficient and annulus appears morphologically normal. Normal forward flow with no regurgitation noted except at the one-week time point. |
|  | 1 | Mild |  |
|  | 4 | None |  |
|  | 24 | None |  |
|  | 32 | None |  |
|  | 40 | None |  |
|  | 48 | None |  |

Figure 7:
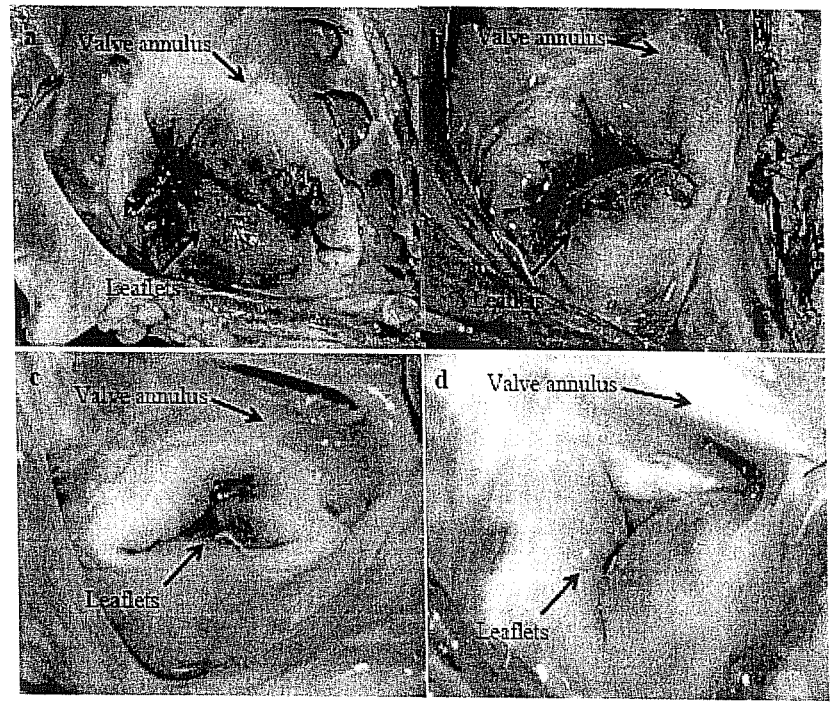
FIG. 7 displays images of a regenerated tri-cuspid valve at various time points following implantation of an exemplary ECM material conduit as described herein.

The replacement valves appeared grossly similar to the native valve that was replaced. FIG. 7 shows 3, 5, 8, and 12-month explants from sheep implanted with the ECM Material Conduit.

Figure 6:
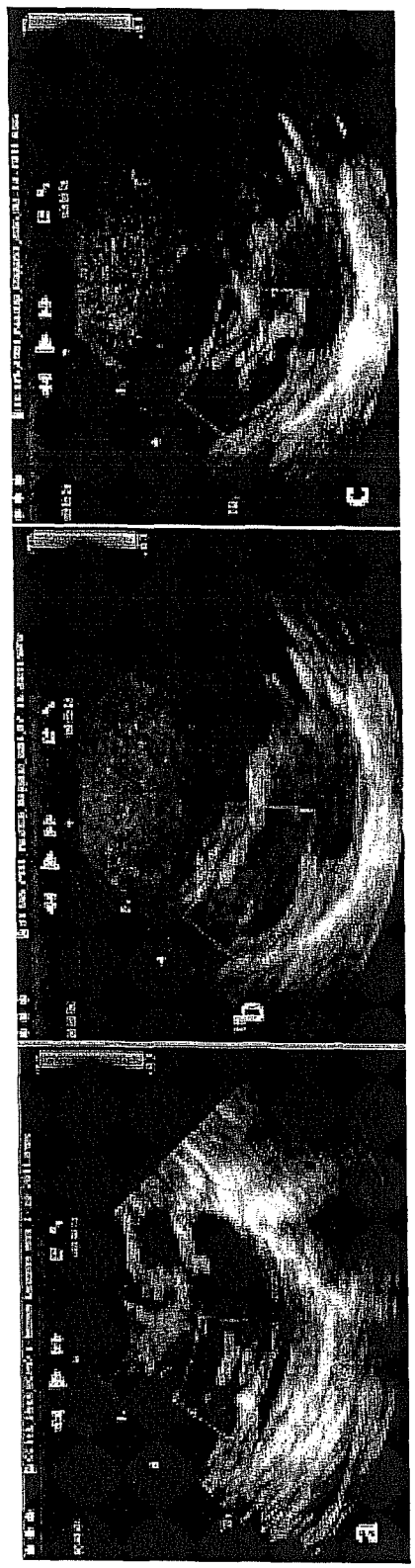
FIG. 6 depicts Doppler echocardiography images taken postoperatively for an exemplary ECM material conduit functioning as a tri-cuspid valve within an animal.

Echocardiography showed good hemodynamics for the valves out to 12 months. Some of these animals exhibited a mild level of backflow through the valve after closure, which was recorded by the echocardiography technician as "mild" or "mild to moderate". Echocardiography showed complete coaptation of the leaflets with no leaflet prolapse (FIG. 6). The degree of apparent valvular insufficiency in these tubular prosthetic valves is exaggerated on echocardiography because of the residual fluid that is trapped within the cylinder when the valves are open. This "closing volume" fluid may be ejected retrograde upon valve closure, which on ECHO would appear to be regurgitant volume when there is no actual regurgitation present.

Figure 8:
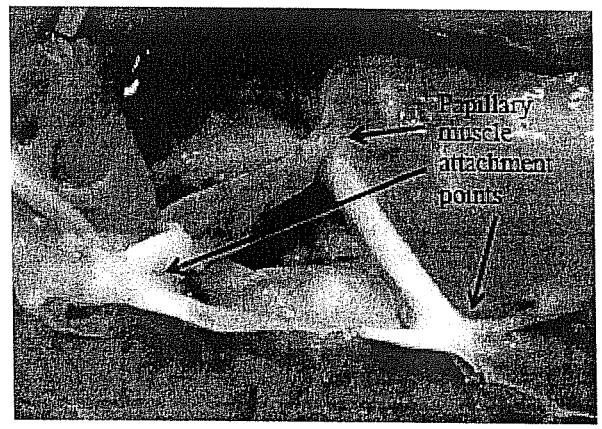
FIG. 8 displays an image of a regenerated tri-cuspid valve at three months following implantation of an exemplary ECM material conduit as described herein.

FIG. 7 shows images of the valve as seen from the right atrium in the closed position demonstrate the progressive remodeling that is occurring over time in the sheep. At the 3-month time point (FIG. 7(a)), remodeling has already occurred at the valve annulus and is extending to the leaflets to regenerate apparently normal valve tissue. At 12 months (FIG. 7(d)), the leaflets have remodeled and appear similar to native valve tissue. Similarly, as shown in FIG. 8, the papillary muscle attachment points are remodeled almost completely at 3 months.

Histology from the sheep at 3, 5, 8, and 12 months following implantation of the CorMatrix ECM Tricuspid Valve stained with a Movat Pentachrome stain was performed. At 3 months, elastin formation was already evident at the valve annulus, and at 5 months elastin was also being generated at the papillary muscle attachment region. By 8 months, the majority of the ECM had been resorbed and remodeled into host tissue. Cells were distributed throughout the valve and the remodeled tissue had faulted a three-layer structure similar to the native valve tissue with elastin in the outer layers and GAGs in the middle.

Example Four

In exemplary applications of the disclosed sterilization and decellularization methods, selected tissues were harvested and rinsed in sterile saline. The selected tissues were then frozen for 24 hours. The frozen tissues were thawed in cold hypotonic tris buffer on ice with 5 mM ethylenediaminetetraacetic acid (EDTA). An extracellular matrix material was then isolated from each selected tissue, as described herein.

The isolated extracellular matrix materials were incubated for 24 to 48 hours in 0.5-1% Triton X-100/0.5-1% Deoxycholic acid with 5 mM EDTA in Dulbecco's Phosphate Buffered Saline (DPBS) (Lonza Walkersville, Inc.). Flat extracellular matrix materials, such as stomach submucosa (SS), small intestinal submucosa (SIS), and bladder submucosa (UBS), were incubated in a stretched configuration. Tubular extracellular matrix materials, such as ureters, arteries, veins, and tubular SIS, were perfused with the solutions through soaking and by use of a peristaltic pump.

After incubation, each extracellular matrix material was rinsed three times with DPBS. Each rinsing with DPBS lasted 30 minutes. Some extracellular matrix materials were then incubated for 2 to 12 hours at 37° C. in isotonic tris buffer containing 10-50 μg/mL of RNAse/0.2-0.5 μg/mL DNAse with 5 mM EDTA. Following this incubation step, the extracellular matrix materials were again rinsed three times with DPBS. Each rinsing with DPBS lasted 30 minutes. The extracellular matrix materials were stored at 4° C.

Within 48 hours of storage, the extracellular matrix materials were processed in supercritical carbon dioxide as disclosed herein for 20-60 minutes at temperatures at or greater than 31.1° C. and pressures at or greater than 1071 psi. After this sterilization step, the extracellular matrix materials were rapidly depressurized at a rate of 2.7 MPa/10 sec. (391.6 psi/10 sec.) for a minute and 19 seconds. During this time, the pressure applied to the extracellular matrix materials rapidly decreased from 9.9 MPa to 0.69 MPa.

The extracellular matrix materials were then processed in supercritical carbon dioxide and peracetic acid (PAA) as disclosed herein for 30 minutes to 6 hours to achieve terminal sterilization. In this processing step, the pressure applied to the extracellular matrix materials was increased to 9.9 MPa. The resulting sterilized, acellular extracellular matrix materials were then packaged in Tyvek® (E.I. du Pont de Nemours & Company) pouches that were sealed within plastic pouches to prevent fluid leakage.

Table 3 summarizes the sterilization and decellularization of porcine ureter, bovine pericardium, and porcine mesothelium.

TABLE 3

| Material | Triton X-100 Conc. | Deoxycholic Acid Conc. | TX-100/ Deoxy incubation | RNAse/ DNase incubation | Supercritical $CO_2$/PAA time |
|---|---|---|---|---|---|
| Porcine ureters | 0.5% | 0.5% | 24 hours | 2 hours | 120 minutes |
| Bovine pericardium | 0.5% | 0.5% | 24 hours | 2 hours | 180 minutes |
| Porcine mesothelium | 0.5% | 0.5% | 24 hours | 2 hours | 120 minutes |

Example Five

The DNA content of ECM material samples was measured as an indicator of decellularization of the respective ECM material samples using various sterilization and decellularization techniques. The measured DNA content was evaluated with a pico green assay in which DNA was labeled with a fluorescent label that was detected with a spectrophotometer. The measured DNA content was normalized by the dry weight of the samples. DNA content was measured and evaluated for the following treatment groups: (1) Lyophilized, non-sterile SIS; (2) Ethylene Oxide (EtO)-sterilized SIS; (3) Lyophilized, non-sterile SIS that was sterilized through a 60 minute treatment with PAA and supercritical $CO_2$, as disclosed herein; (4) Lyophilized, non-sterile SIS that was sterilized through a 20 minute treatment with PAA and supercritical $CO_2$, as disclosed herein; and (5) Raw, unprocessed SIS.

Figure 9:
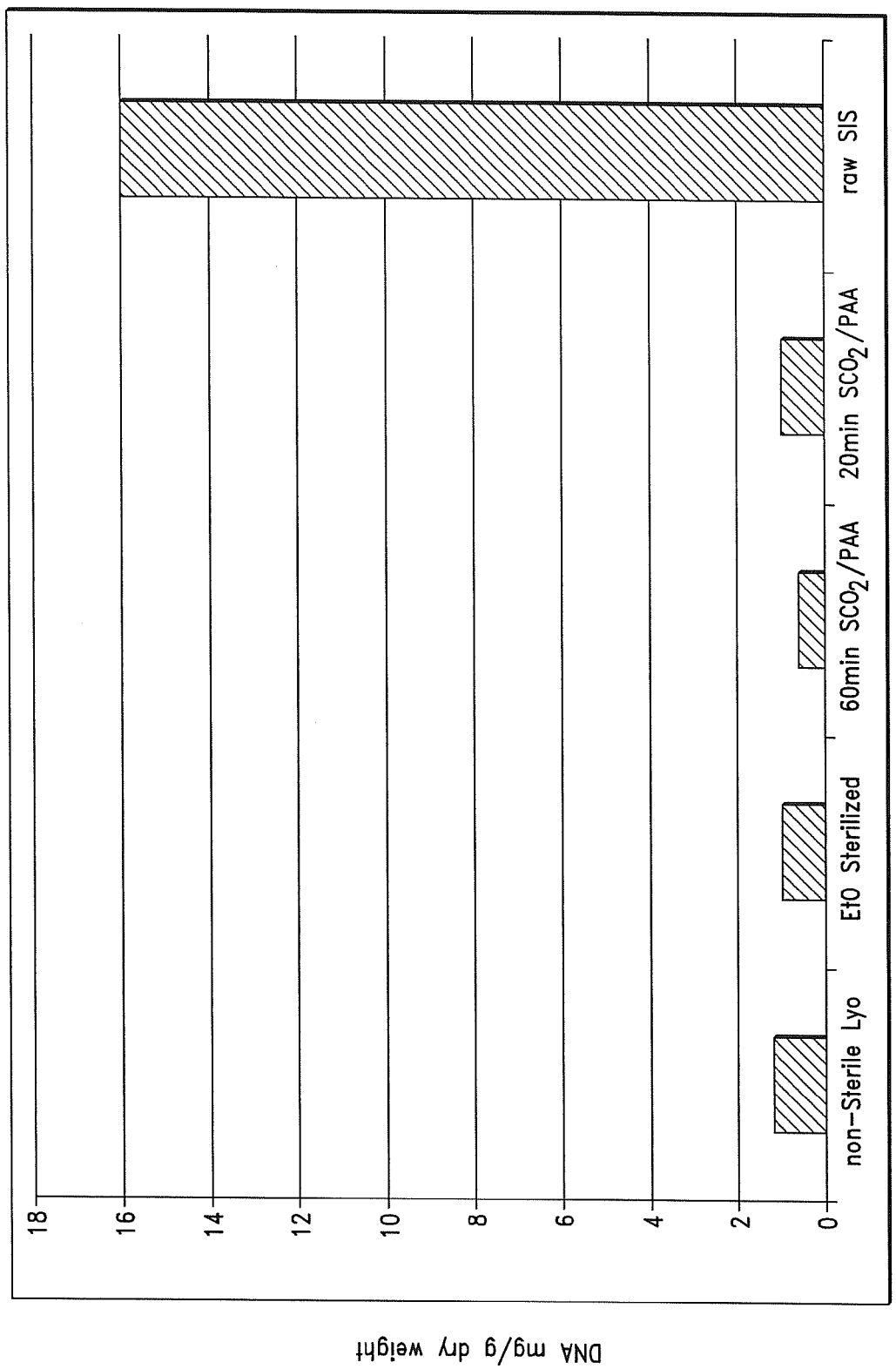
FIGS. 9-10 depict the results of an experiment in which DNA content was measured for small intestinal submucosa (SIS) compositions following various sterilization methods, including the sterilization methods described herein.
Figure 10:
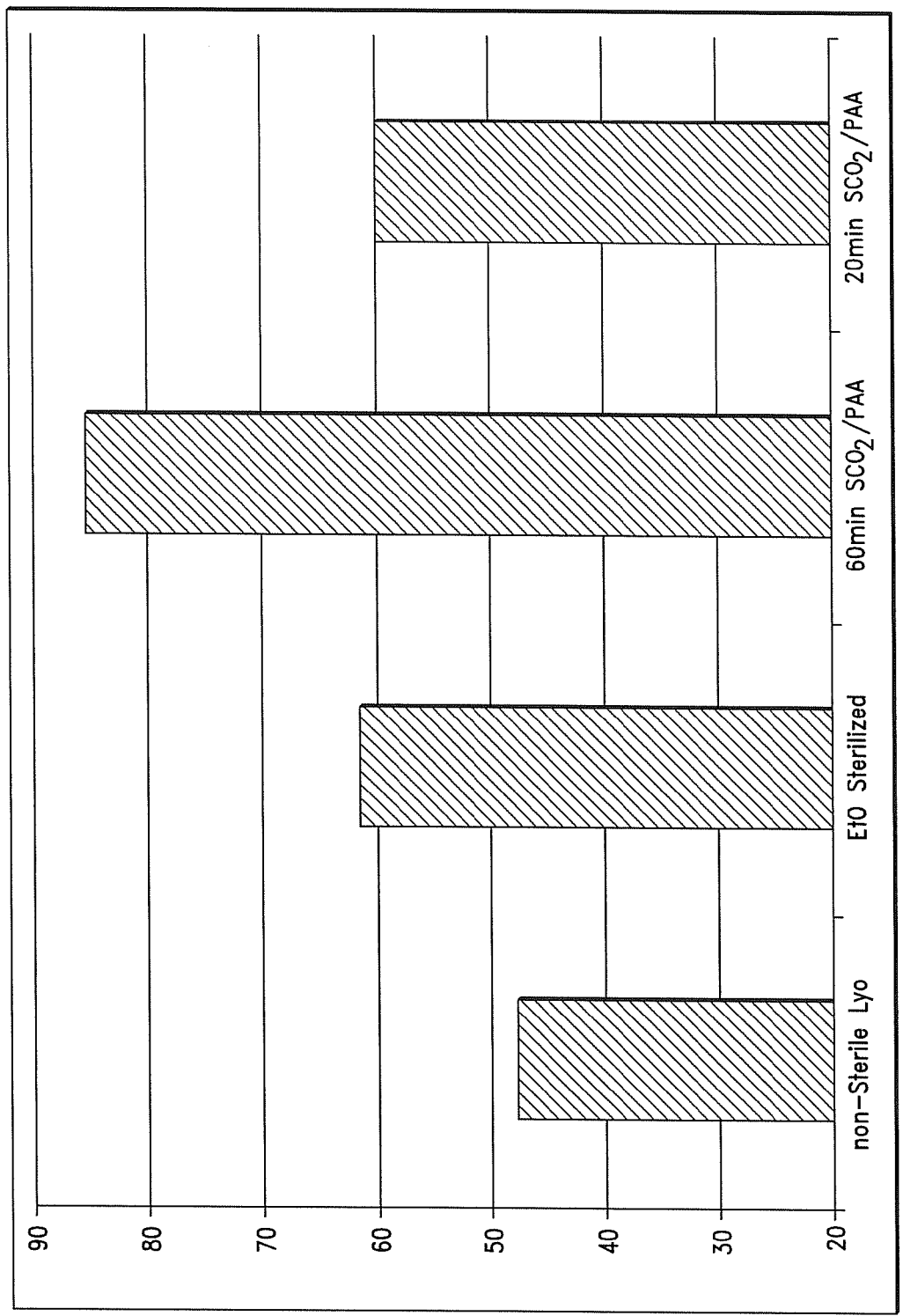

FIG. 9 shows the total DNA content for the respective samples, as normalized by dry weight. FIG. 10 shows the percent of DNA that was removed from each respective sample, as compared to raw, unprocessed SIS. These results indicated that by sterilizing the non-sterile SIS using a 60 minute treatment with PAA and supercritical $CO_2$, as disclosed herein, over 96% of the DNA found in raw SIS was removed, as compared to only 94% when the SIS was sterilized by EtO and only 93% when the SIS was not sterilized by any method.

Example Six

Ureters were processed with a gentle detergent (0.5% Triton X-100/0.5% Sodium Deoxycholate in 5 mM EDTA in DPBS) for 24 hours and then rinsed three times in DPBS as disclosed herein. After this pretreatment, the ureters were decellularized and sterilized using rapid depressurization and treatment with PAA and supercritical $CO_2$, as disclosed herein. Hematoxylin and Eosin (H&E) Stains were prepared for one sample ureter at the following stages of treatment: (A) native ureter; (B) pretreated ureter; and (C) pretreated ureter with rapid depressurization and treatment with PAA and supercritical $CO_2$, as disclosed herein. These stains indicated that DNA content was significantly reduced with rapid depressurization.

Example Seven

Figure 11:
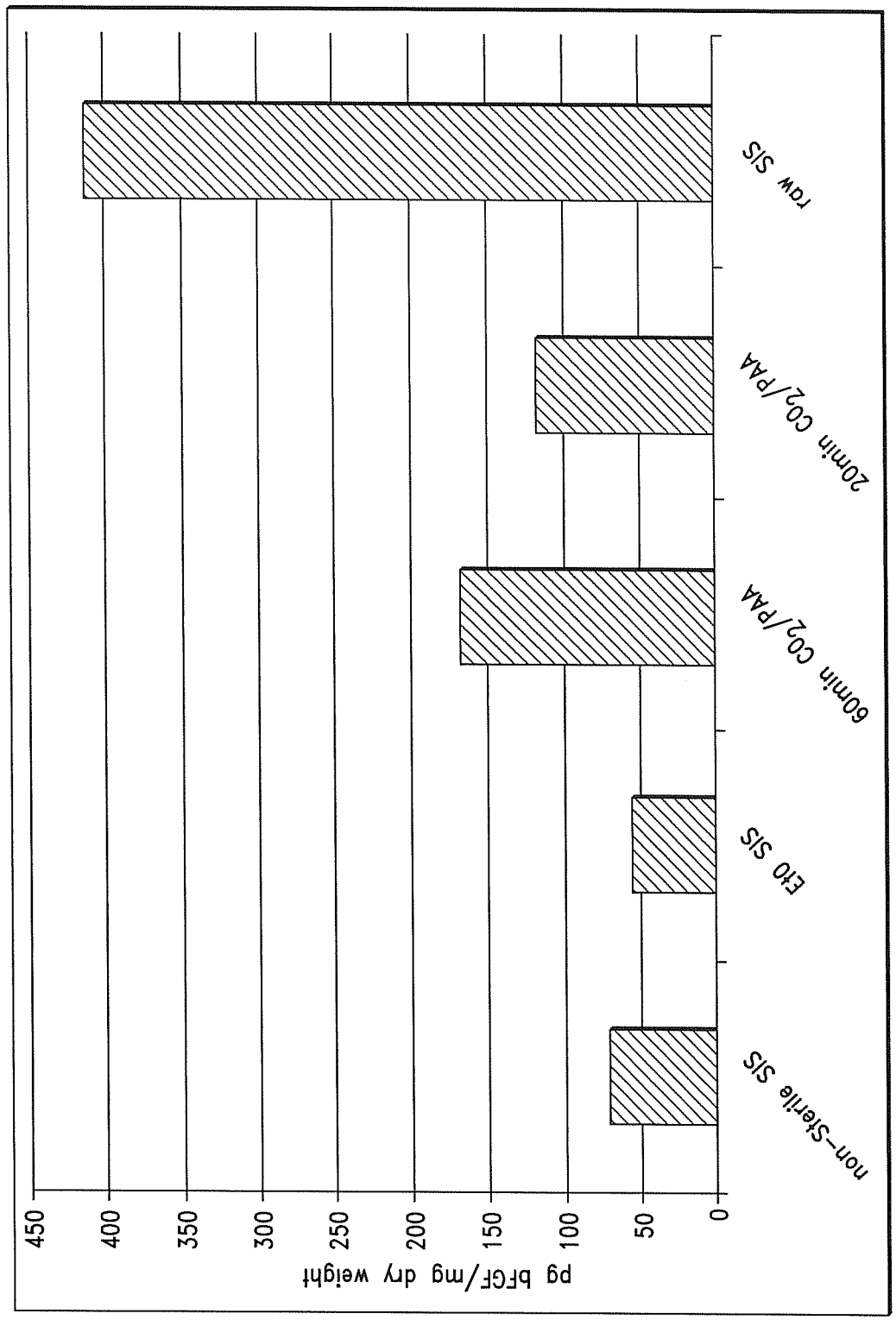
FIGS. 11-12 depict the results of an experiment in which native growth factor content was measured for SIS compositions following various sterilization methods, including the sterilization methods described herein.
Figure 12:
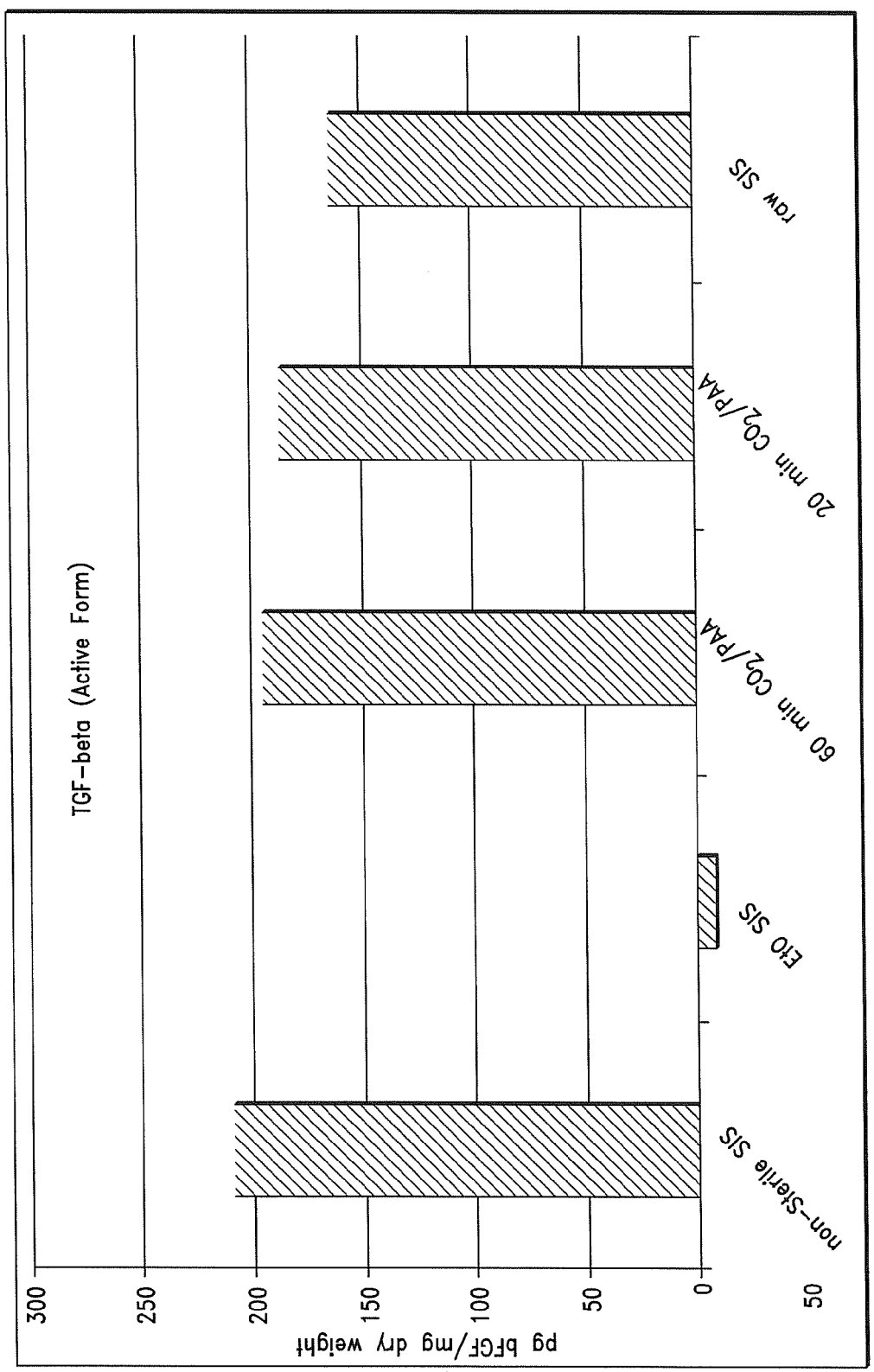

The growth factor content of ECM material samples was measured. Enzyme-linked immunosorbent (ELISA) assays were performed on the ECM material samples to quantify the content of bFGF and the active form of TGF-.beta. in each respective sample. The following treatment groups were evaluated: (1) Lyophilized, non-sterile SIS; (2) Ethylene Oxide (EtO)-sterilized SIS; (3) Lyophilized, non-sterile SIS that was sterilized through a 60 minute treatment with PAA and supercritical $CO_2$, as disclosed herein; (4) Lyophilized, non-sterile SIS that was sterilized through a 20 minute treatment with PAA and supercritical $CO_2$, as disclosed herein; and (5) Raw, unprocessed SIS. The bFGF content and TGF-$\beta$. content measurements were normalized by dry weight of each respective sample. These results are shown in FIGS. 11 and 12. These results indicated that the concentration of both growth factors was reduced by exposure to EtO. However, the concentration of the growth factors was not affected by sterilization with PAA and supercritical $CO_2$.

Example Eight

Figure 13:
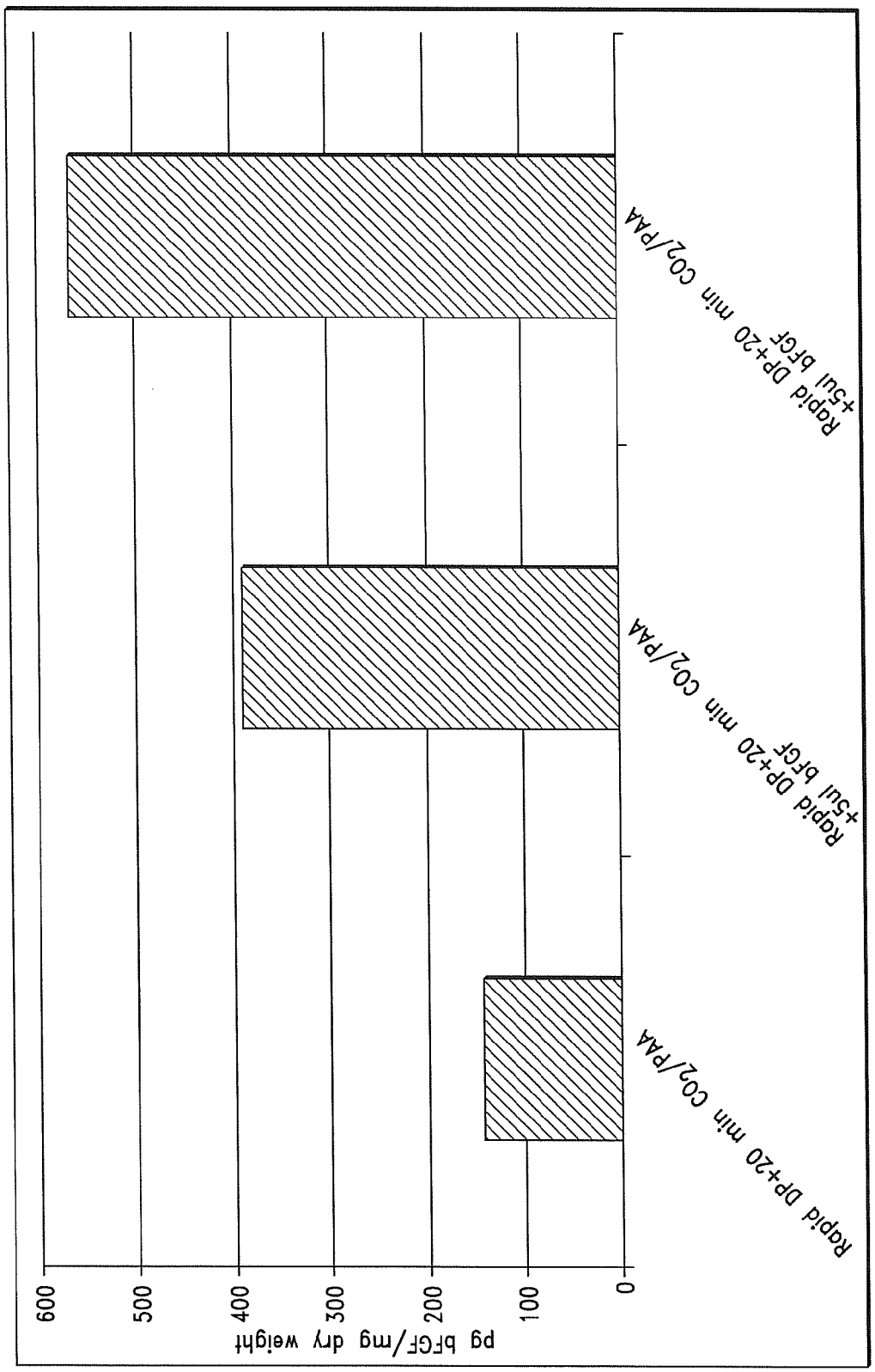
FIG. 13 depicts the results of an experiment in which bFGF was incorporated into SIS compositions during rapid depressurization, as described herein.

Using the methods disclosed herein, supercritical $CO_2$ was used as a primary sterilant and as a carrier for adding bFGF into SIS sheets. First, the respective SIS sheets were placed into Tyvek® pouches along with varying amounts of bFGF. The pouches were exposed to supercritical $CO_2$ for 60 minutes at 9.6 MPa. The pouches were rapidly depressurized at a rate of 7.20 MPa/min. Samples were directly processed in 16 mL PAA in supercritical $CO_2$ for 20 minutes. The following treatment groups were evaluated: (1) No bFGF added; (2) 5 μL bFGF added; and (3) 15 μL bFGF added. Each .mu.L of bFGF contained 0.1 μg of bFGF. Thus, since each SIS sheet weighed approximately 0.5 g, the maximum concentrations of bFGF for the 5 μL and 15 μL groups were about 4170 pg/mg dry weight and about 12,500 pg/mg dry weight, respectively. The bFGF content for these groups is shown in FIG. 13, as measured with respect to the dry weight of the respective samples. These results indicated that the measured concentrations of bFGF did not reach the maximum concentrations and that the sample to which 15 μL of bFGF was added did not have a measured concentration of bFGF that was three times greater than the measured concentration of bFGF in the sample to which 5 μL of bFGF was added.

Example Nine

Figure 14:
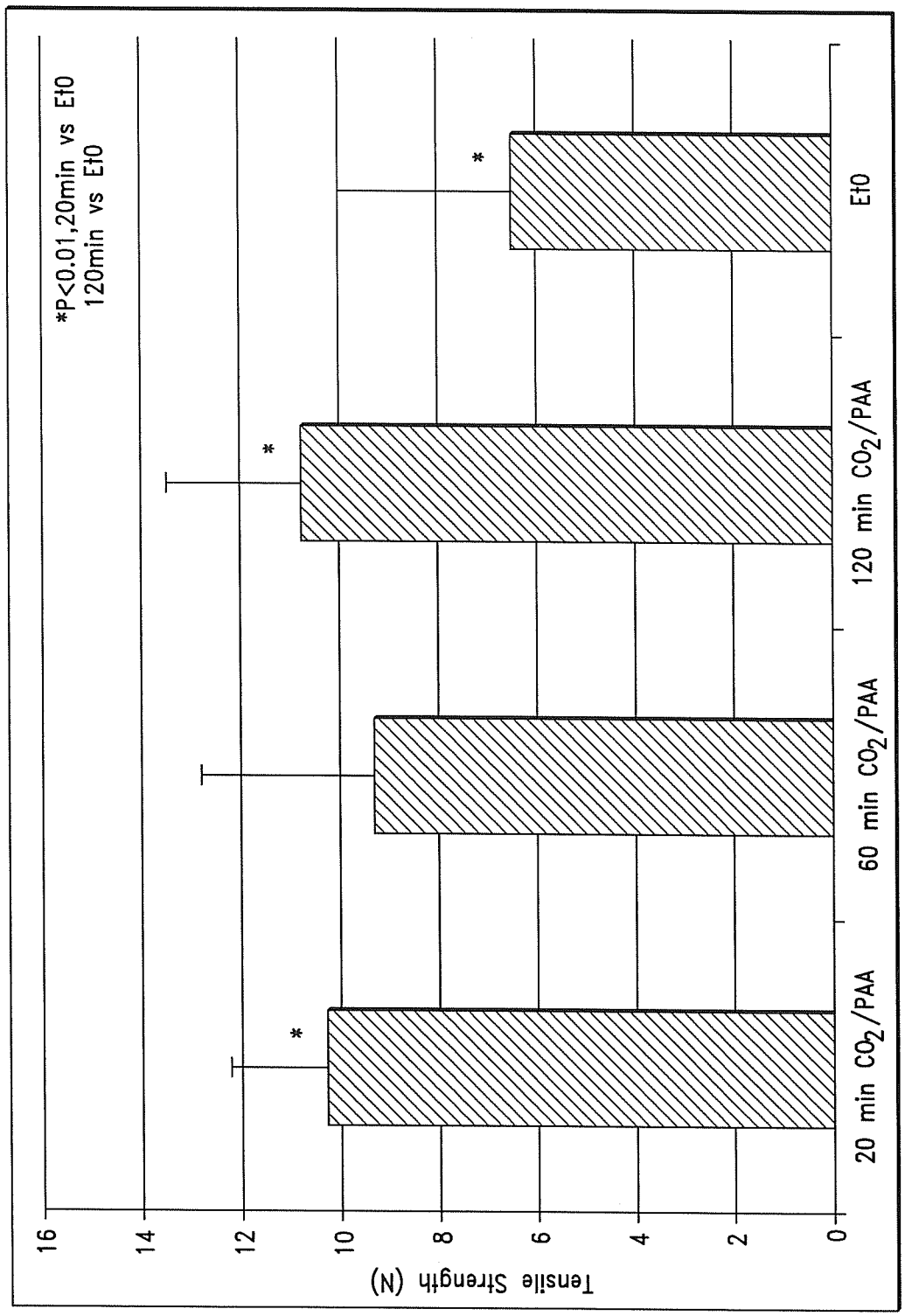
FIG. 14 depicts the results of an experiment in which the tensile strength of two-ply SIS compositions was measured following various sterilization methods, including the sterilization methods described herein.

The tensile strengths of two-ply SIS samples were measured. The following treatment groups were evaluated: (1) EtO Treatment; (2) PAA/supercritical $CO_2$ treatment for 20 minutes; (3) PAA/supercritical $CO_2$ treatment for 60 minutes; and (4) PAA/supercritical $CO_2$ treatment for 120 minutes. The tensile strength test results are shown in FIG. 14. These results indicated that the SIS samples that were processed with PAA/supercritical $CO_2$ for 20 or 120 minutes, as disclosed herein, were significantly stronger than the SIS samples that were processed with EtO.

Example Ten

Rapid depressurization was used following gentle detergent soaks or perfusion of the ECM materials listed in Table 4 (below) at the noted concentrations and for the noted time periods. Tissues were harvested and rinsed in saline. The tissues were frozen for at least 24 hours. The tissues were thawed in cold hypotonic tris buffer on ice with 5 mM EDTA. The ECM of interest was isolated. For flat tissues (e.g., stomach submucosa, small intestine submucosa, and bladder submucosa), the tissue was stretched on a tissue stretching device and incubated in solutions in a stretched configuration. For tubular tissues (e.g., ureters, arteries, veins, and tubular SIS), the tissue was perfused with solutions using a peristaltic pump and were soaked during incubation. The tissues were incubated for 2 to 24 hours in 0.5% Triton X-100/0.5% Deoxycholic acid with 5 mM EDTA in DPBS. The tissues were rinsed 3 times for 15-30 minutes each time in DPBS. The tissues were stored at 4° C. Within 48 hours of tissue storage, the tissues were processed in supercritical $CO_2$ for 20-120 minutes followed by rapid depressurization (RDP) (decrease in pressure from 9.9 MPa to 0.69 MPa in 1 min 19 sec, corresponding to a depressurization of 2.7 MPa/10 sec).

TABLE 4

| Material | Triton X-100 Conc. | Deoxycholic Acid Con. | TX-100/ Deoxy incubation | Supercritical $CO_2$ time |
| --- | --- | --- | --- | --- |
| Porcine ureters | 0.5% | 0.5% | 24 hours | 60 minutes |
| Bovine pericardium | 0.5% | 0.5% | 24 hours | 60 minutes |
| Porcine mesothelium | 0.5% | 0.5% | 24 hours | 60 minutes |
| SIS | 0.5% | 0.5% | 24 hours | 60 minutes |

The results showed that supercritical $CO_2$ exposure followed by rapid depressurization ($SCCO_2$+RDP) did aid in the removal of cell remnants and DNA while preserving growth factors in the ECMs.

Example Eleven

The growth factor content of various ECM compositions was analyzed using basic fibroblast growth factor (bFGF) as a representative growth factor. bFGF was selected because it is a prevalent growth factor in native ECM tissues. An enzyme-linked immunosorbent assay (ELISA, R&D Systems, Minneapolis, Minn.) was used to measure the bFGF content in the following samples: (1) Unprocessed (Raw) SIS; (2) SIS after detergent soak (TX-deoxy) only; (3) SIS after TX-deoxy and RDP (includes $SCCO_2$); (4) SIS after TX-deoxy, RDP, and PAA ($SCCO_2$ with PAA for sterilization); (5) SIS after TX-deoxy, and PAA; (6) SIS sterilized by EtO (supplied by Cook Biotech, Inc.); and (7) non-sterile SIS (supplied by Cook Biotech, Inc.).

Figure 15:
FIG. 15 depicts the results of an experiment in which native growth factor content was measured for SIS compositions following various sterilization and/or decellularization methods, including the sterilization and decellularization methods described herein.
Figure 16:
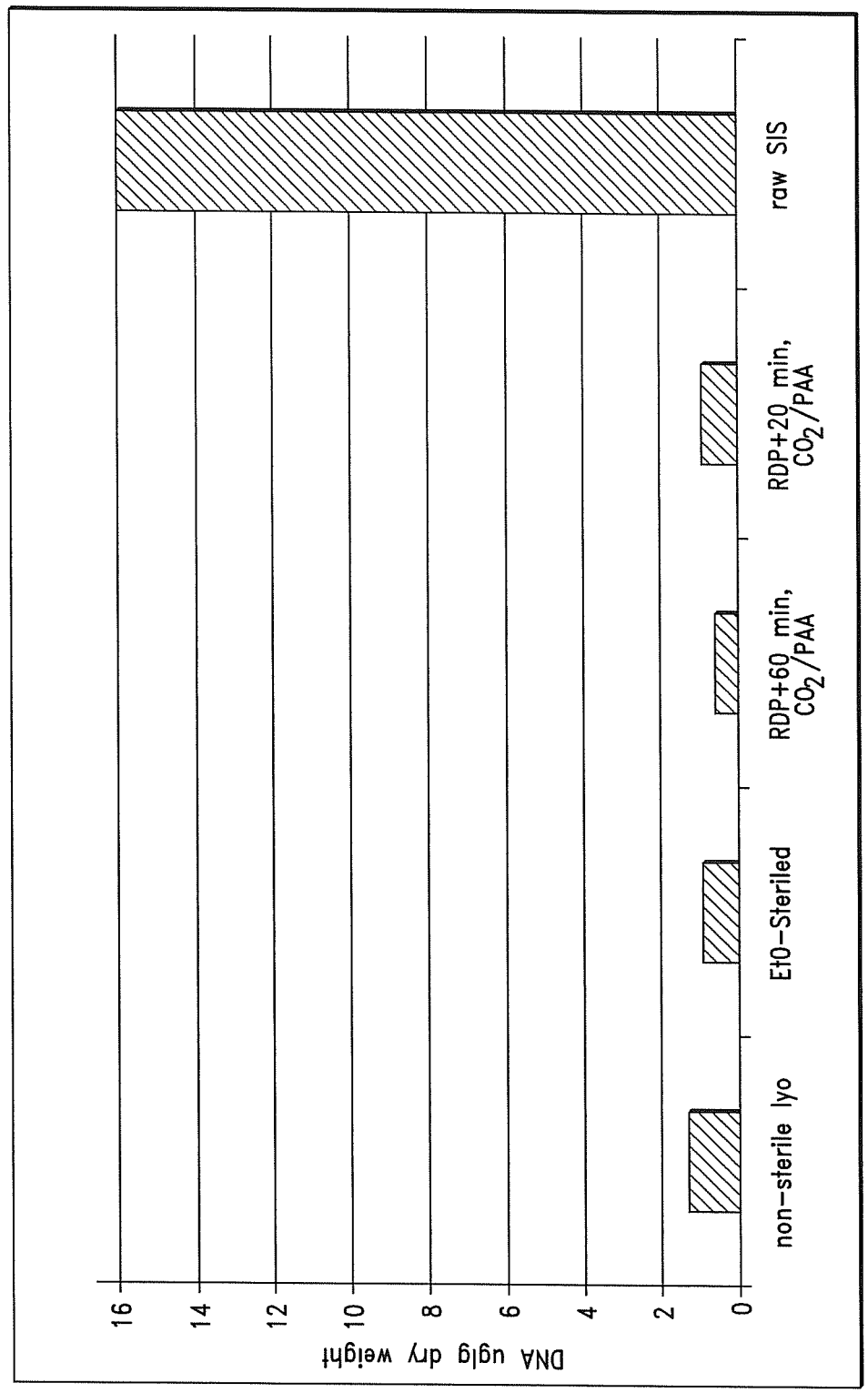
FIG. 16 shows the DNA content in SIS after it is processed in various ways. The baseline measurement is raw. The tissue was then exposed to supercritical CO.sub.2 followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 17:
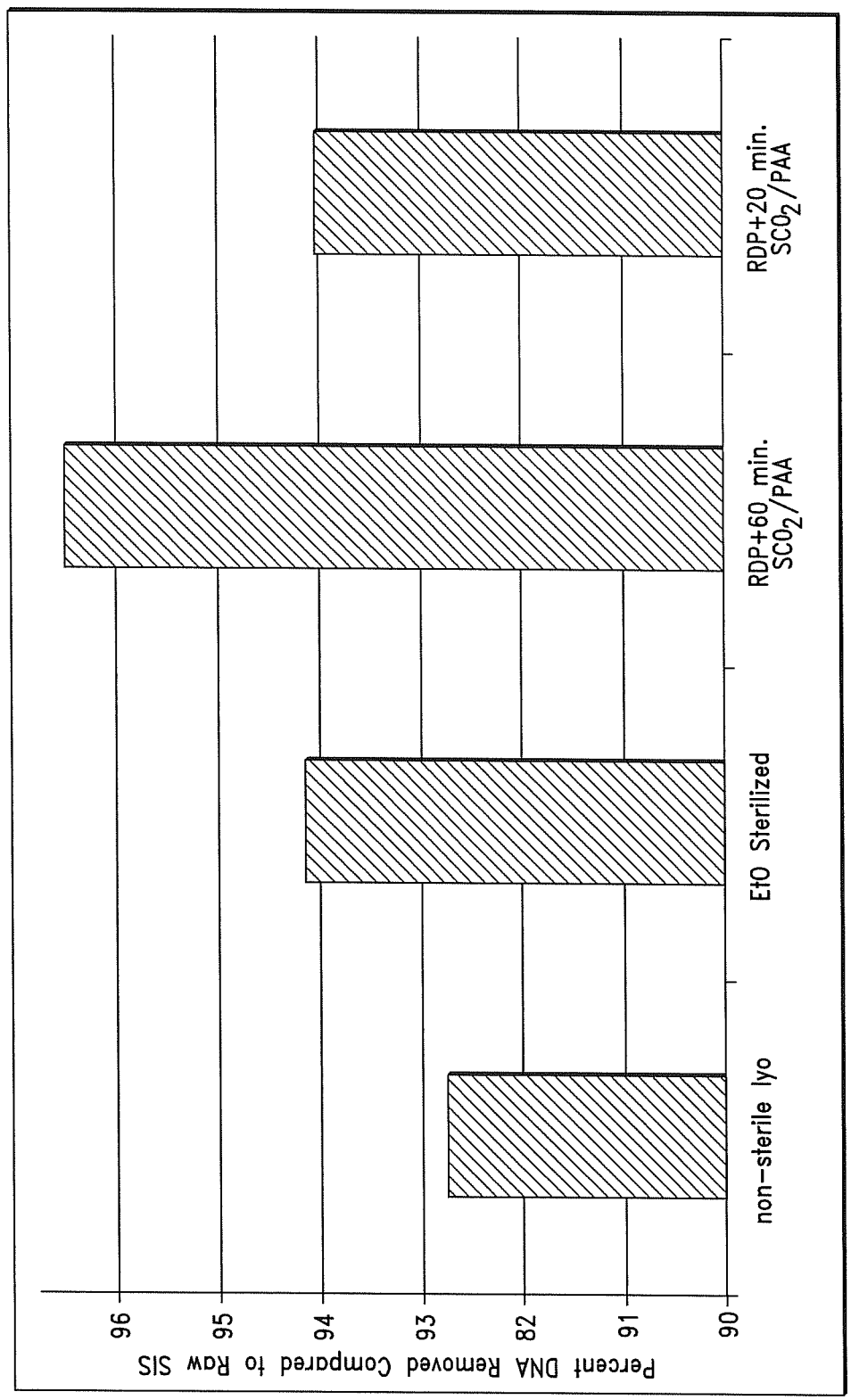
FIG. 17 shows the Percent removal of DNA from SIS after it is processed in various ways. The baseline measurement is raw. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 18:
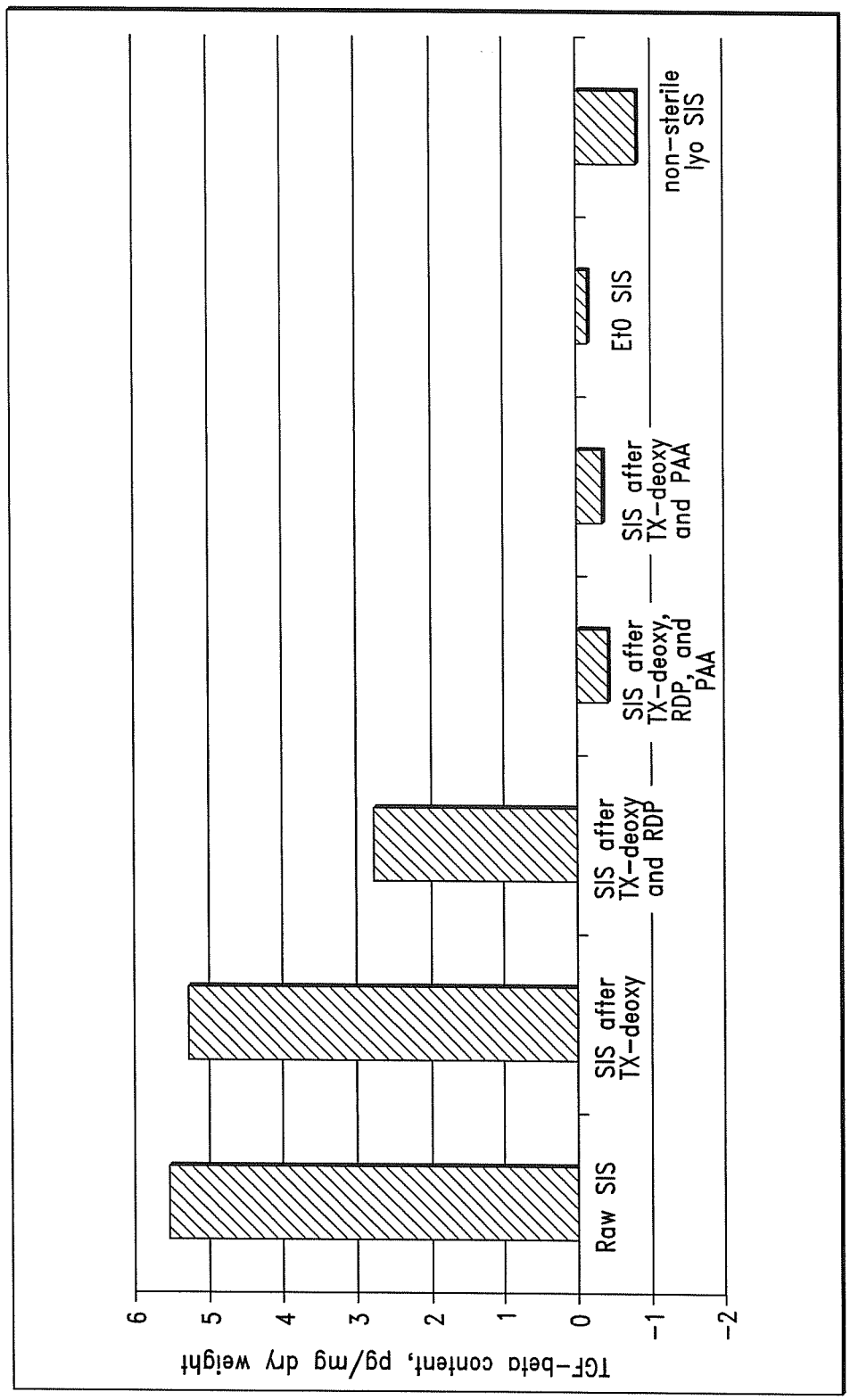
FIG. 18 shows the variable active Transforming Growth Factor (TGF-beta) content in SIS after it is processed in various ways. The baseline measurement is raw, or unprocessed SIS followed by processing with only Triton X-100 (TX-100) detergent. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 19:
FIG. 19 shows the variable basic Fibroblast Growth Factor (bFGF) content in SIS after it is processed in various ways. The baseline measurement is raw, or unprocessed SIS followed by processing with only Triton X-100 (TX-100) detergent. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 20:
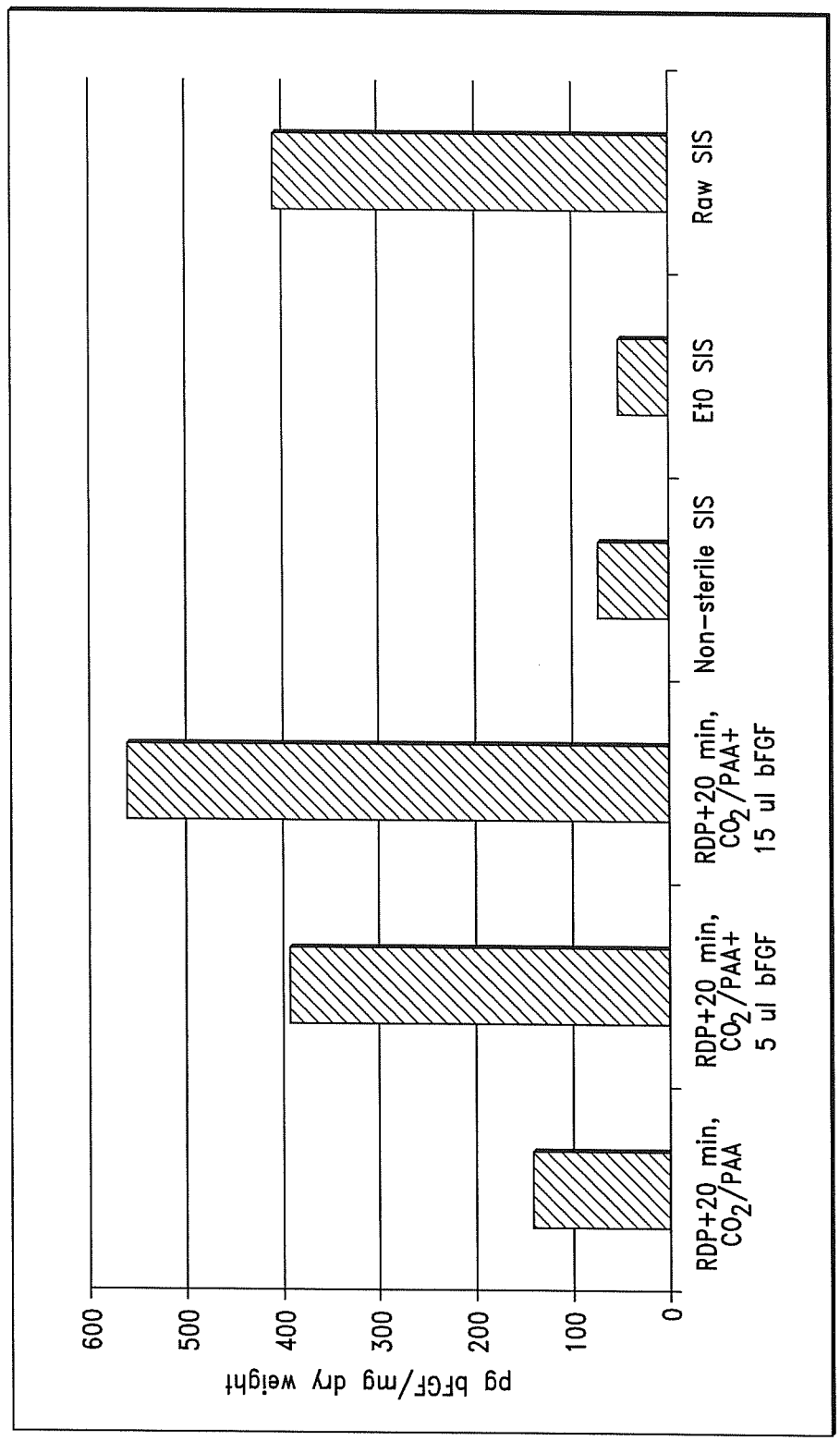
FIG. 20 shows the addition of basic Fibroblast Growth Factor (bFGF) content to SIS using rapid depressurization. The baseline measurement is raw, or unprocessed SIS. The comparison is to processed SIS either unsterilized or sterilized with ethylene oxide (ETO).

In these studies, SIS was used to compare an ECM composition processed with and without RDP to SIS provided by Cook Biotech, Inc. Some of the processed SIS was also sterilized using the described $SCCO_2$+PAA method after decellularization. The measured growth factor content of the respective ECM compositions is shown in FIG. 15.

These results indicate that the rapid depressurization process was more effective than other decellularization processes at preserving the bFGF content and that the additional RDP processing to remove residual DNA and cell fragments results in only a small loss of bFGF. By comparison, the PAA sterilization process appeared to remove almost all of the remaining bFGF, even in the absence of RDP. Additionally, the rapid depressurization process preserved more of the bFGF content in the native SIS than the Cook decellularization methods. For purposes of these results, when the bFGF content was reduced, it is assumed that all other growth factor content was similarly reduced since the growth factors are all bound to the ECM compositions in a similar manner.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A valve conduit for regenerating an atrioventricular (AV) valve to replace a defective AV valve within a heart of a subject, the AV valve being adapted to be attached to an annular region of the heart, the defective AV valve comprising first cardiovascular tissue, the defective AV valve further comprising a first plurality of valve leaflets, comprising:
   a bioabsorbable tubular conduit comprising sterile, acellular small intestine submucosa (SIS), said SIS comprising less than 4% DNA content and a dry weight bFGF content of at least 140 pg/mg of said SIS, said SIS further exhibiting at least 96% decellurization and a tensile strength of at least 9 N,
   said SIS further comprising an exogenously added growth factor selected from the group consisting of transforming growth factor alpha (TGF-alpha), transforming growth factor beta (TGF-beta), fibroblast growth factor-2 (FGF-2), basic fibroblast growth factor (bFGF) and vascular epithelial growth factor (VEGF),
   said tubular conduit defining a lumen and having an inlet portion and an outlet portion, said inlet portion of said tubular conduit being configured to attach to said annular region of said heart of said subject, said outlet portion of said tubular conduit being configured to attach to papillary muscles within said subject's heart,
   said tubular conduit member being configured to induce generation of a plurality of regenerated valve leaflets in said tubular conduit member lumen when said tubular conduit member is coupled to said first cardiovascular tissue of said annular region,
   said plurality of regenerated valve leaflets comprising second cardiovascular tissue, said second cardiovascular tissue and said first cardiovascular tissue being similar, said plurality of regenerated valve leaflets being configured to function in a manner similar to said first plurality of valve leaflets of said defective AV valve.

2. A valve conduit for regenerating an atrioventricular (AV) valve to replace a defective AV valve within a heart of a subject, the AV valve being adapted to be attached to an annular region of the heart, the defective AV valve comprising first cardiovascular tissue, the defective AV valve further comprising a first plurality of valve leaflets, comprising:

a bioabsorbable tubular conduit comprising sterile, acellular small intestine submucosa (SIS), said SIS comprising less than 4% DNA content and a dry weight bFGF content of at least 140 pg/mg of said SIS, said SIS further exhibiting at least 96% decellurization and a tensile strength of at least 9 N, said SIS further comprising an exogenously added statin selected from the group consisting of atorvastatin, cerivastatin, fluvastatin, lovastatin, mevastatin, pitavastatin, pravastatin, rosuvastatin and simvastatin, said tubular conduit defining a lumen and having an inlet portion and an outlet portion, said inlet portion of said tubular conduit being configured to attach to said annular region of said heart of said subject, said outlet portion of said tubular conduit being configured to attach to papillary muscles within said subject's heart, said tubular conduit member being configured to induce generation of a plurality of regenerated valve leaflets in said tubular conduit member lumen when said tubular conduit member is coupled to said first cardiovascular tissue of said annular region, said plurality of regenerated valve leaflets comprising second cardiovascular tissue, said second cardiovascular tissue and said first cardiovascular tissue being similar, said plurality of regenerated valve leaflets being configured to function in a manner similar to said first plurality of valve leaflets of said defective AV valve.

* * * * *